United States Patent
Momose

(10) Patent No.: US 9,916,710 B2
(45) Date of Patent: Mar. 13, 2018

(54) COIN-SHAPED DETECTION OBJECT DISCRIMINATING DEVICE

(71) Applicant: NIDEC SANKYO CORPORATION, Suwa-gun, Nagano (JP)

(72) Inventor: Shogo Momose, Nagano (JP)

(73) Assignee: NIDEC SANKYO CORPORATION, Suwa-Gun, Nagano (JP)

( * ) Notice: Subject to any disclaimer, the term of this patent is extended or adjusted under 35 U.S.C. 154(b) by 74 days.

(21) Appl. No.: 14/905,076

(22) PCT Filed: Apr. 7, 2014

(86) PCT No.: PCT/JP2014/060072
§ 371 (c)(1),
(2) Date: Jan. 14, 2016

(87) PCT Pub. No.: WO2015/008513
PCT Pub. Date: Jan. 22, 2015

(65) Prior Publication Data
US 2016/0163141 A1    Jun. 9, 2016

(30) Foreign Application Priority Data
Jul. 18, 2013  (JP) .................. 2013-149163

(51) Int. Cl.
*G01R 33/12*    (2006.01)
*G07D 5/08*    (2006.01)
*G01N 1/00*    (2006.01)
*H01F 1/00*    (2006.01)

(52) U.S. Cl.
CPC ............... *G07D 5/08* (2013.01); *G01N 1/00* (2013.01); *G01N 2201/00* (2013.01); *H01F 1/00* (2013.01)

(58) Field of Classification Search
CPC ........ G01N 1/00; G01N 2201/00; H01F 1/00; G07D 1/00; G07D 2201/00
See application file for complete search history.

(56) References Cited

U.S. PATENT DOCUMENTS 4,124,110 A * 11/1978 Hovorka .................. G07D 5/08
                                                                  194/318
4,334,604 A *  6/1982 Davies .................... G07D 5/08
                                                                  194/319

(Continued)

FOREIGN PATENT DOCUMENTS

EP    2626839 A1 *  8/2013  ............... G07D 5/08
JP    2003021620 A     1/2003

(Continued)

OTHER PUBLICATIONS

International Search Report corresponding to Application No. PCT/JP2014/060072; dated Apr. 28, 2014, with English translation.

*Primary Examiner* — Jermele M Hollington
*Assistant Examiner* — Temilade Rhodes-Vivour
(74) *Attorney, Agent, or Firm* — Cantor Colburn LLP

(57) ABSTRACT

A coin-shaped detection object discriminating device may be used with a detection object in a coin shape, and the coin-shaped detection object discriminating device may include a passage through which the detection object is passed; a permanent magnet; and a magnetic sensor disposed opposite to the permanent magnet across the passage.

10 Claims, 12 Drawing Sheets

(56) References Cited

U.S. PATENT DOCUMENTS

| | | | | |
|---|---|---|---|---|
| 6,250,453 B1 * | 6/2001 | Furuya | ............ | G07D 1/00 |
| | | | | 194/317 |
| 6,640,955 B1 * | 11/2003 | Furuya | ............ | G07D 5/08 |
| | | | | 194/317 |
| 2004/0119470 A1 * | 6/2004 | Yajima | ............ | G01V 3/105 |
| | | | | 324/253 |
| 2004/0207391 A1 * | 10/2004 | Momose | ............ | G01B 7/023 |
| | | | | 324/207.17 |

FOREIGN PATENT DOCUMENTS

| JP | 2008293337 A | 12/2008 |
|---|---|---|
| JP | 2009072300 A | 4/2009 |
| JP | 2015019776 A | 2/2015 |

* cited by examiner

COIN-SHAPED DETECTION OBJECT DISCRIMINATING DEVICE

CROSS REFERENCE TO RELATED APPLICATIONS

This is the U.S. national stage of application No. PCT/JP2014/060072, filed on Apr. 7, 2014. Priority under 35 U.S.C. §119(a) and 35 U.S.C. §365(b) is claimed from Japanese Applications No. 2013-149163, filed Jul. 18, 2013; the disclosure of which is incorporated herein by reference.

FIELD OF THE INVENTION

At least an embodiment of the present invention relates to a coin-shaped detection object discriminating device for discriminating authenticity, a defective or the like of a coin-shaped detection object.

BACKGROUND

Conventionally, a token selector used in a slot machine has been known (see, for example, Patent Literature 1). The token selector described in Patent Literature 1 is a device for sorting tokens inserted into a token input port and it discharges a fraudulent token whose size is small to a token receiving tray and sends out a normal token to a token tank. The token selector is formed with a token passage through which a token inserted into the token inlet port is passed and the token is sorted by utilizing the token passage in this token selector.

PATENT LITERATURE

[PTL 1] Japanese Patent Laid-Open No. 2009-72300

In recent years, in shops where slot machines are installed, there is a need for using a plurality of kinds of tokens whose outer diameters and thicknesses are the same as each other but whose magnetic permeabilities are different from each other as authentic tokens in the same shop. In other words, there is a need for using a token having a certain magnetic permeability as an authentic token in slot machines installed in a certain area and, in slot machines installed in another area in the same shop, a token whose outer diameter and thickness are the same but whose magnetic permeability is different is also used as an authentic token. For example, in the same shop, there is a need for using a nonmagnetic token formed of nonmagnetic material as an authentic token in slot machines installed in a certain area and, in slot machines installed in another area, a token whose outer diameter and thickness are the same is used as an authentic token which is formed of nonmagnetic material whose surface is treated with metal plating such as nickel plating, or a token having magnetism such as a token formed of soft magnetic material is used as an authentic token.

However, the token selector described in Patent Literature 1 is unable to discriminate and sort a plurality of kinds of tokens whose magnetic permeabilities are different from each other when outer diameters and thicknesses of tokens are the same.

SUMMARY

In view of the problem described above, at least an embodiment of the present invention provides a coin-shaped detection object discriminating device structured to discriminate authenticity, a defective or the like of a coin-shaped detection object, the coin-shaped detection object discriminating device being capable of discriminating a plurality of kinds of detection objects whose outer diameters and thicknesses are the same but whose magnetic permeabilities are different from each other.

In order to attain the above, at least an embodiment of the present invention provides a coin-shaped detection object discriminating device including a passage which is formed in an inside of the device so that a detection object in a coin shape is passed and a permanent magnet and a magnetic sensor which are oppositely disposed to each other across the passage.

The coin-shaped detection object discriminating device in accordance with at least an embodiment of the present invention includes a permanent magnet and a magnetic sensor which are oppositely disposed to each other across a passage where a coin-shaped detection object is passed. Therefore, according to at least an embodiment of the present invention, even in a case that outer diameters and thicknesses of a plurality of kinds of detection objects passing through the passage are the same as each other, when their magnetic permeabilities are different from each other, a difference occurs between variation amounts of output levels of the magnetic sensor when detection objects are passed through the passage depending on kinds of the detection objects. For example, a difference occurs between a variation amount of an output level of the magnetic sensor when a nonmagnetic detection object is passed through the passage and a variation amount of an output level of the magnetic sensor when a detection object having magnetism is passed through the passage. Therefore, in at least an embodiment of the present invention, a plurality of kinds of tokens whose outer diameters and thicknesses are the same but whose magnetic permeabilities are different from each other can be discriminated.

In at least an embodiment of the present invention, it is preferable that the coin-shaped detection object discriminating device includes a core body formed of soft magnetic material which includes a first core disposed on one side in a thickness direction of the detection object passing through the passage and a second core disposed on the other side in the thickness direction of the detection object, the first core is formed with a first protruded part which is protruded toward the second core, the second core is formed with a second protruded part which is protruded toward the first protruded part, the permanent magnet is disposed between the passage and the first protruded part in the thickness direction of the detection object, and the magnetic sensor is disposed between the passage and the second protruded part in the thickness direction of the detection object. According to this structure, density of magnetic flux generated from the permanent magnet and passing through the magnetic sensor can be increased by the first protruded part and the second protruded part. Therefore, discrimination accuracy for a detection object can be enhanced.

In at least an embodiment of the present invention, it is preferable that, when a direction perpendicular to a passing direction of the detection object and the thickness direction of the detection object is referred to as an orthogonal direction, the core body is formed in a ring shape which is provided with the first core, the second core, a first connecting core connecting one end of the first core with one end of the second core in the orthogonal direction, and a second connecting core connecting the other end of the first core with the other end of the second core in the orthogonal direction. According to this structure, leakage of magnetic flux generated by the permanent magnet from the core body can be reduced. Therefore, density of the magnetic flux generated from the permanent magnet and passing through the magnetic sensor can be increased effectively and, as a result, discrimination accuracy for a detection object can be enhanced effectively. Further, according to this structure, the core body can be functioned as a magnetic shield and lowering of discrimination accuracy for a detection object caused by an external magnetic field can be suppressed.

In at least an embodiment of the present invention, the magnetic sensor is, for example, one of a magnetoresistance effect element, a magnetic impedance element, a Hall element and a flux gate element.

In at least an embodiment of the present invention, it is preferable that the coin-shaped detection object discriminating device includes an excitation coil, a detection coil, a third core formed of soft magnetic material which is disposed on one side in the thickness direction of the detection object and around which one of the excitation coil and the detection coil is wound, and a fourth core formed of soft magnetic material which is disposed on the other side in the thickness direction of the detection object and around which the other of the excitation coil and the detection coil is wound. According to this structure, an outer diameter, thickness and/or material and the like of a detection object can be discriminated on the basis of an output of the detection coil.

In at least an embodiment of the present invention, it is preferable that the coin-shaped detection object discriminating device includes a case body in which the permanent magnet, the magnetic sensor, the excitation coil, the detection coil, the third core and the fourth core are accommodated, and the excitation coil, the detection coil, the third core and the fourth core are held by the case body at a shifted position from the permanent magnet and the magnetic sensor in a passing direction of the detection object. According to this structure, a detection mechanism structured of the permanent magnet, the magnetic sensor and the like and a detection mechanism structured of the excitation coil, the detection coil and the like can be held by a common case body. Therefore, a structure of the coin-shaped detection object discriminating device can be simplified.

In at least an embodiment of the present invention, it is preferable that the coin-shaped detection object discriminating device includes a control section which is connected with the magnetic sensor and the detection coil, the magnetic sensor is disposed on an upstream side relative to the detection coil in the passing direction of the detection object, and a sensor output signal in an analog shape generated on the basis of an output of the magnetic sensor and a coil output signal in an analog shape generated on the basis of an output of the detection coil are inputted into the control section. In a case that a signal level of the coil output signal becomes larger when the detection object is passed through the passage, the control section discriminates the detection object by using the magnetic sensor based on a difference between one of a peak value and a bottom value of the sensor output signal and a value of the sensor output signal when a signal level of the coil output signal becomes not more than a predetermined threshold value. In a case that a signal level of the coil output signal becomes smaller when the detection object is passed through the passage, the control section discriminates the detection object by using the magnetic sensor based on a difference between one of a peak value and a bottom value of the sensor output signal and a value of the sensor output signal when a signal level of the coil output signal becomes not less than a predetermined threshold value.

According to this structure, based on a difference between a value of the sensor output signal immediately after a detection object has passed through between the permanent magnet and the magnetic sensor and a peak value or a bottom value of the sensor output signal, the detection object can be discriminated by using the magnetic sensor. Therefore, even when a signal level of the sensor output signal in a standby state that no detection object is existed between the permanent magnet and the magnetic sensor is varied due to variation of ambient temperature around the detection object discriminating device, the variation can be canceled and, as a result, the detection object can be discriminated with a high degree of accuracy.

In at least an embodiment of the present invention, it is preferable that the coin-shaped detection object discriminating device includes an excitation coil which is wound around one of the first protruded part and the second protruded part, and a detection coil which is wound around the other of the first protruded part and the second protruded part. According to this structure, an outer diameter, thickness and/or material and the like of a detection object can be discriminated on the basis of an output of the detection coil. Further, according to this structure, an excitation coil and a detection coil are wound around a core body for increasing density of magnetic flux passing through the magnetic sensor and thus, in comparison with a case that another core around which an excitation coil and a detection coil are wound is provided in addition to the core body, a structure of the coin-shaped detection object discriminating device can be simplified.

In at least an embodiment of the present invention, it is preferable that, when a direction perpendicular to a passing direction of the detection object and the thickness direction of the detection object is referred to as an orthogonal direction, a third protruded part which is protruded toward the second core is formed on both sides in the orthogonal direction of the first protruded part of the first core, a fourth protruded part which is protruded toward the third protruded part is formed on both sides in the orthogonal direction of the second protruded part of the second core, a first detection coil as the detection coil is wound over the first protruded part and the third protruded parts, a second detection coil as the detection coil is wound around the first protruded part, and the excitation coil is wound over the second protruded part and the fourth protruded parts. According to this structure, an outer diameter of a detection object is mainly discriminated by using the first detection coil and material and thickness of the detection object can be mainly discriminated by using the second detection coil.

When a metal detection object is passed through between the permanent magnet and the magnetic sensor, an eddy current is generated in the detection object. Therefore, when a nonmagnetic detection object is passed through between the permanent magnet and the magnetic sensor, a signal level of an analog-shaped sensor output signal generated on the basis of an output of the magnetic sensor is varied due to influence of the eddy current. On the other hand, when a detection object having magnetism is passed through between the permanent magnet and the magnetic sensor, a signal level of the sensor output signal is varied due to influence of a shield by the detection object between the permanent magnet and the magnetic sensor and influence of the eddy current. A peak value and a bottom value of a signal level of the sensor output signal which is varied due to only influence of an eddy current is varied depending on a speed of a detection object passing through the passage.

In a case that a nonmagnetic detection object is passed through between the permanent magnet and the magnetic sensor, if an external factor such as an ambient temperature around the coin-shaped detection object discriminating device does not vary, a signal level of the sensor output signal when the centers of the permanent magnet and the magnetic sensor and the center of a detection object are coincided with each other in a passing direction of the detection object becomes equal to a signal level of the sensor output signal in a standby state that no detection object is existed between the permanent magnet and the magnetic sensor. Further, when the centers of the excitation coil and the detection coil and the center of a detection object are coincided with each other in a passing direction of the detection object, a signal level of the analog-shaped coil output signal generated on the basis of an output of the detection coil becomes a peak value or a bottom value. Therefore, in a case that the excitation coil is wound around one of the first protruded part and the second protruded part and the detection coil is wound around the other of the first protruded part and the second protruded part, when the centers of the permanent magnet and the magnetic sensor and the center of a detection object are coincided with each other in the passing direction of the detection object, a signal level of the coil output signal becomes a peak value or a bottom value.

Accordingly, in at least an embodiment of the present invention, it is preferable that the coin-shaped detection object discriminating device includes a control section which is connected with the magnetic sensor and the detection coil, a sensor output signal in an analog shape generated on the basis of an output of the magnetic sensor and a coil output signal in an analog shape generated on the basis of an output of the detection coil are inputted into the control section and, in a case that a signal level of the coil output signal becomes larger when the detection object is passed through the passage, the control section discriminates the detection object by using the magnetic sensor based on a value of the sensor output signal at the time of a peak of the signal level of the coil output signal and, in a case that a signal level of the coil output signal becomes smaller when the detection object is passed through the passage, the control section discriminates the detection object by using the magnetic sensor based on a value of the sensor output signal at the time of a bottom of the signal level of the coil output signal. According to this structure, even when a peak value and a bottom value of a signal level of the sensor output signal varied due to influence of an eddy current is varied depending on a speed of a detection object passing through the passage, it can be discriminated whether the detection object is provided with magnetism or not by judging whether or not a signal level of the sensor output signal at the time of a peak or a bottom of a signal level of the coil output signal is equal to a signal level of the sensor output signal in a standby state. Therefore, it can be easily discriminated whether a detection object is provided with magnetism or not.

As described above, in at least an embodiment of the present invention, in a coin-shaped detection object discriminating device structured to discriminate authenticity, a defective or the like of a coin-shaped detection object, the coin-shaped detection object discriminating device is capable of discriminating a plurality of kinds of detection objects whose outer diameters and thicknesses are the same but whose magnetic permeabilities are different from each other.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DESCRIPTION OF EMBODIMENTS

Embodiments of the present invention will be described below with reference to the accompanying drawings.
(Schematic Structure of Coin-Shaped Detection Object Discriminating Device)

Figure 1:
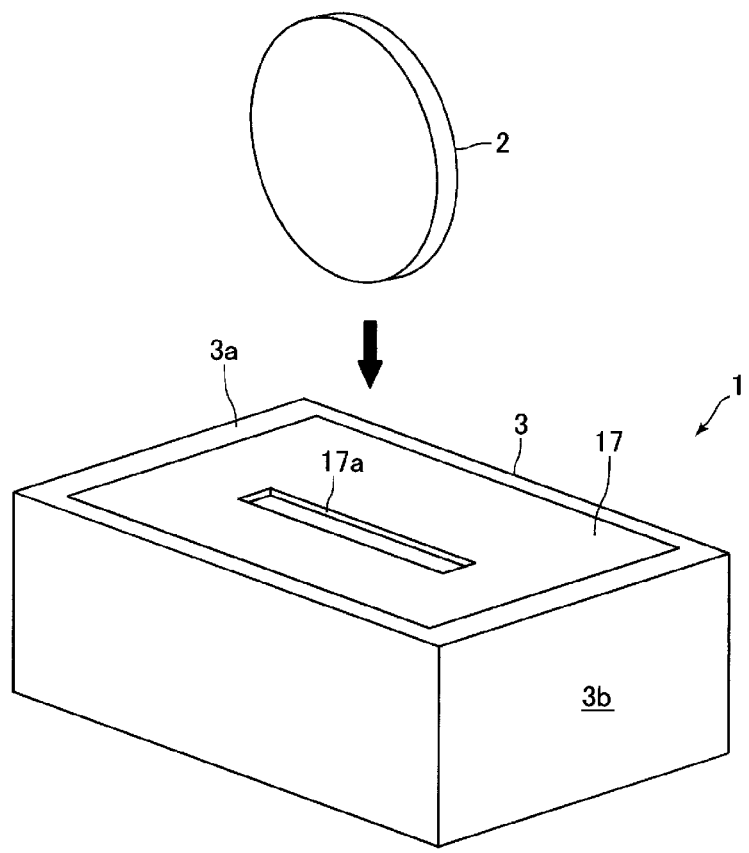
FIG. 1 is a perspective view showing a coin-shaped detection object discriminating device in accordance with an embodiment of the present invention.
Figure 1:
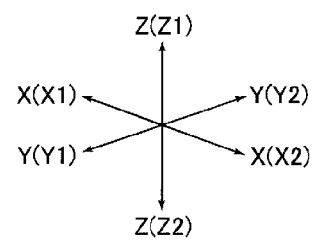
Figure 2:
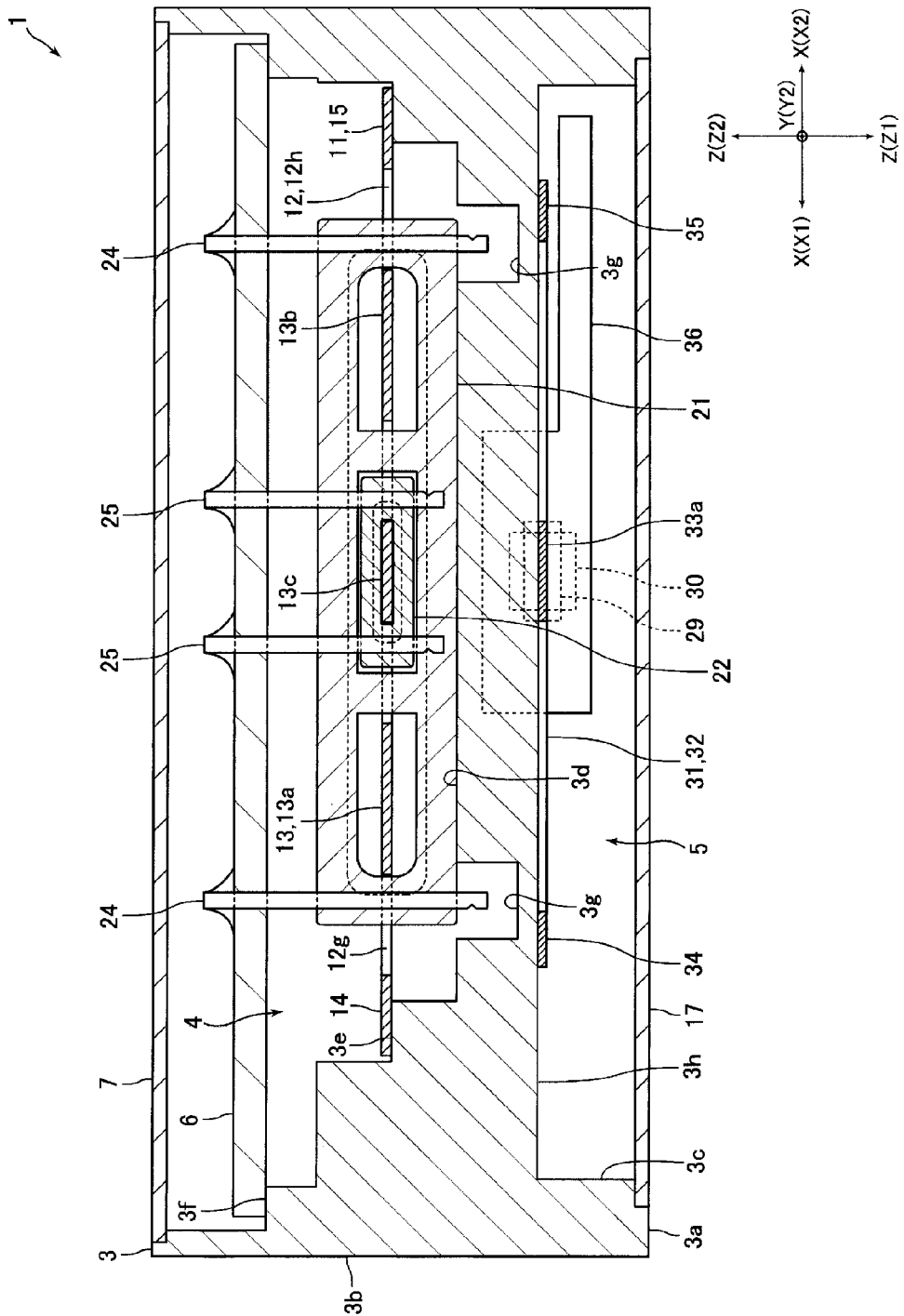
FIG. 2 is a vertical cross-sectional view showing the coin-shaped detection object discriminating device in FIG. 1 which is reversed in an upper and lower direction.
Figure 3:
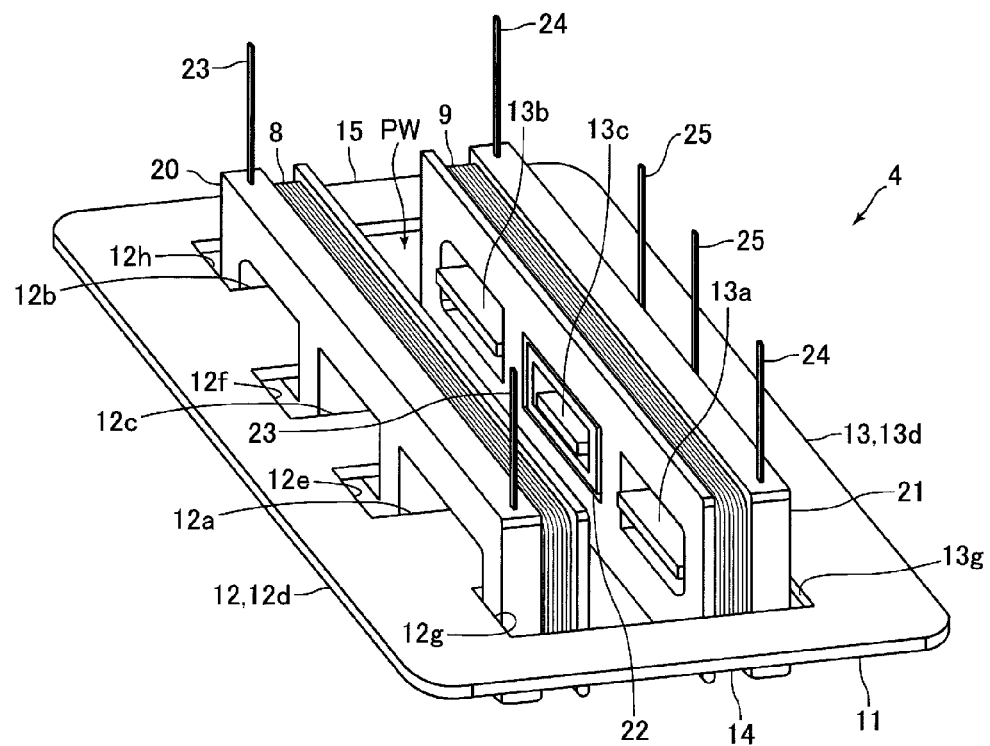
FIG. 3 is a perspective view showing a first detection mechanism in FIG. 2 which is viewed from its bottom face side.
Figure 3:
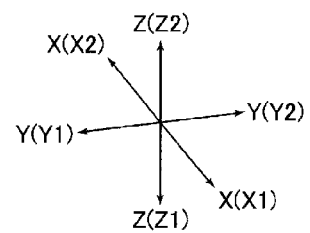

FIG. 1 is a perspective view showing a coin-shaped detection object discriminating device 1 in accordance with an embodiment of the present invention. FIG. 2 is a vertical cross-sectional view showing the coin-shaped detection object discriminating device 1 in FIG. 1 which is reversed in an upper and lower direction. FIG. 3 is a perspective view showing a first detection mechanism 4 in FIG. 2 which is viewed from its bottom face side.

A coin-shaped detection object discriminating device 1 in this embodiment is a device for discriminating authenticity of a token 2 which is a coin-shaped detection object, or a device for discriminating whether an authentic token 2 is a non-defective product or a defective product (in other words, whether or not an authentic token 2 is a defective due to abrasion or deformation). The coin-shaped detection object discriminating device 1 is mounted on and used in a slot machine (not shown). In other words, the coin-shaped detection object discriminating device 1 in this embodiment is a device for discriminating authenticity or the like of a token 2 which is inserted into a token inlet port of a slot machine. Therefore, in the following description, a coin-shaped detection object discriminating device 1 in this embodiment is referred to as a "token discriminating device 1". The token discriminating device 1 includes, as shown in FIGS. 1 and 2, a case body 3 and a first detection mechanism 4 and a second detection mechanism 5 accommodated in the case body 3. A passage PW through which a token 2 is passed is formed in an inside of the token discriminating device 1. A token 2 is formed of metal material. Further, the token 2 is formed in a circular plate shape.

In the following description, as shown in FIG. 1 and the like, respective three directions perpendicular to each other are referred to as an "X" direction, a "Y" direction and a "Z" direction, and the "X" direction is set to be a right and left direction, the "Y" direction is set to be a front and rear direction, and the "Z" direction is set to be an upper and lower direction. Further, an "X1" direction side is a "right" side, an "X2" direction side is a "left" side, a "Y1" direction side is a "front" side, a "Y2" direction side is a "rear" (back) side, a "Z1" direction side is an "upper" side, and a "Z2" direction side is a "lower" side. In this embodiment, a token 2 is passed through the passage PW from an upper side to a lower side. In other words, the upper and lower direction is a passing direction of a token 2 which is passed through the passage PW.

The case body 3 is formed of resin material. The case body 3 is formed in a substantially rectangular parallelepiped box shape having an upper face part 3*a* structuring an upper face of the case body 3 and a side face part 3*b* structuring four side faces on front and rear sides and right and left sides of the case body 3. An under face of the case body 3 is opened. An opening portion of an under face of the case body 3 is covered by a cover member 7. The cover member 7 is formed in a thin flat plate shape. Further, a circuit board 6 is fixed to a lower end side in an inside of the case body 3. The upper face part 3*a* is formed with a recessed part 3*c* which is recessed from an upper face of the upper face part 3*a* to a lower side. The recessed part 3*c* is covered by a cover member 17. The cover member 17 is formed in a thin flat plate shape. In this embodiment, a first detection mechanism 4 is disposed to a lower side of the upper face part 3*a* and a second detection mechanism 5 is disposed in the recessed part 3*c*.

The cover member 17 is formed with a passage opening 17*a* (see FIG. 1) in a slit shape through which a token 2 is passed. The upper face part 3*a*, the circuit board 6 and the cover member 7 are also formed with passage openings in a slit shape through which a token 2 is passed. The passage openings formed in the upper face part 3*a*, the circuit board 6 and the cover member 7 and the passage opening 17*a* structure a part of the passage PW. A guide member (not shown) for guiding a token 2 to the passage opening 17*a* is fixed to the case body 3.

The circuit board 6 is a rigid circuit board such as a glass epoxy substrate and is formed in a substantially rectangular flat plate shape. The circuit board 6 is formed with a conductor pattern made of conductive material such as a copper foil. The circuit board 6 is disposed in an inside of the case body 3 so that its thickness direction is coincided with the upper and lower direction and covers an under face of the first detection mechanism 4. The cover member 17 is formed of metal. Outer side faces on the front and rear sides and the right and left sides of four side faces structuring the side face part 3*b* are fixed with a thin metal plate (not shown) formed in a flat plate shape. The circuit board 6, the cover member 17 and the metal plates fixed to the side face part 3*b* function as an electromagnetic shield for protecting the first detection mechanism 4 and the second detection mechanism 5 from an external electromagnetic wave around the token discriminating device 1.

(Structures of First Detection Mechanism and Second Detection Mechanism)

Figure 4:
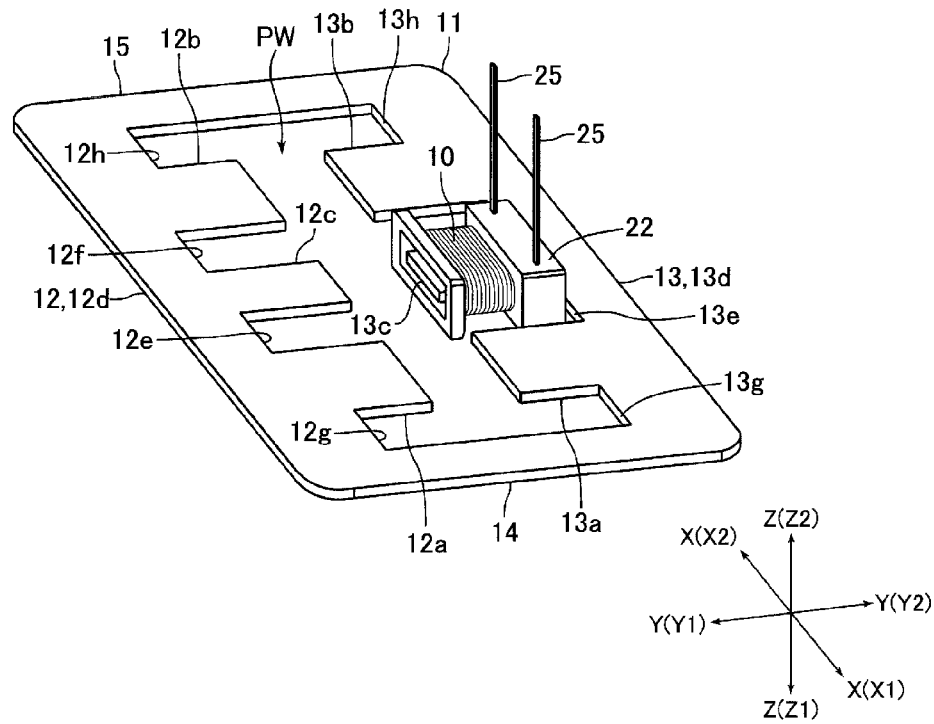
FIG. 4 is a perspective view showing a state that an excitation coil, a detection coil and bobbins are detached from the state shown in FIG. 3.
Figure 5:
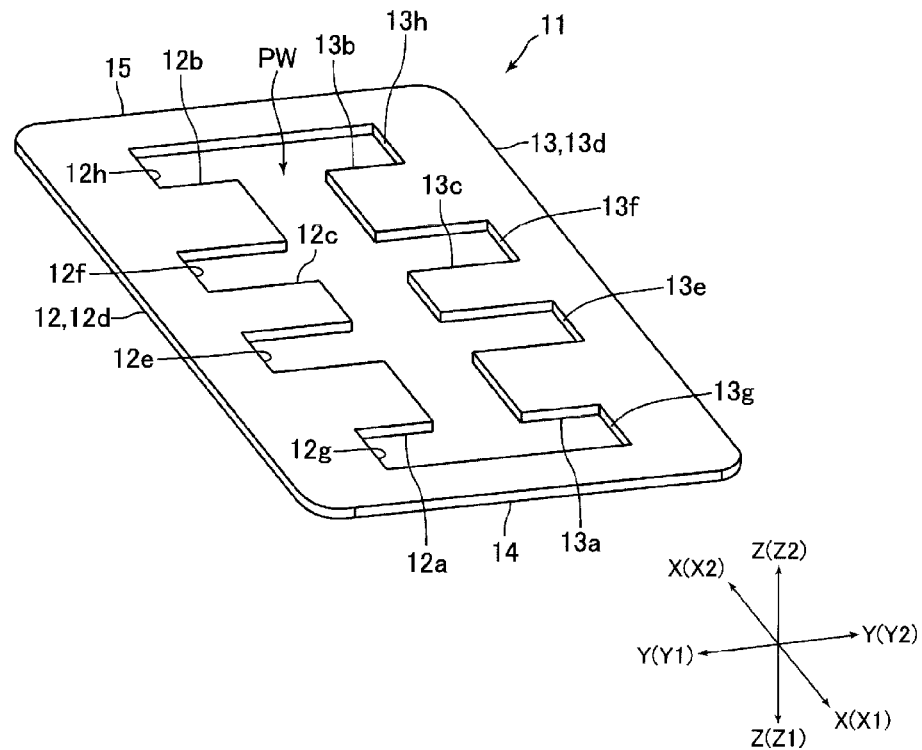
FIG. 5 is a perspective view showing a ring-shaped core in FIG. 3.
Figure 6:
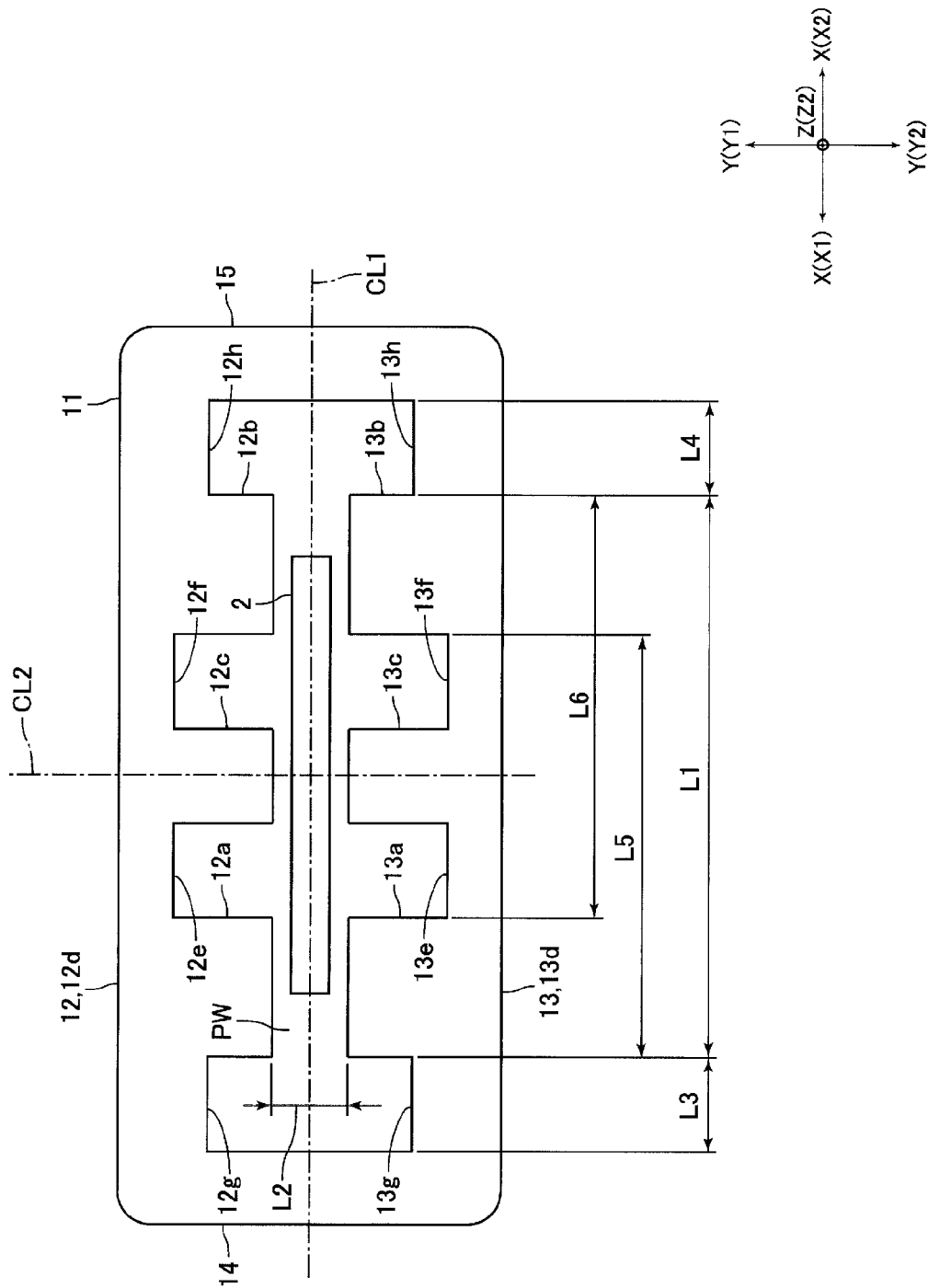
FIG. 6 is a bottom view showing the ring-shaped core in FIG. 3.
Figure 7:
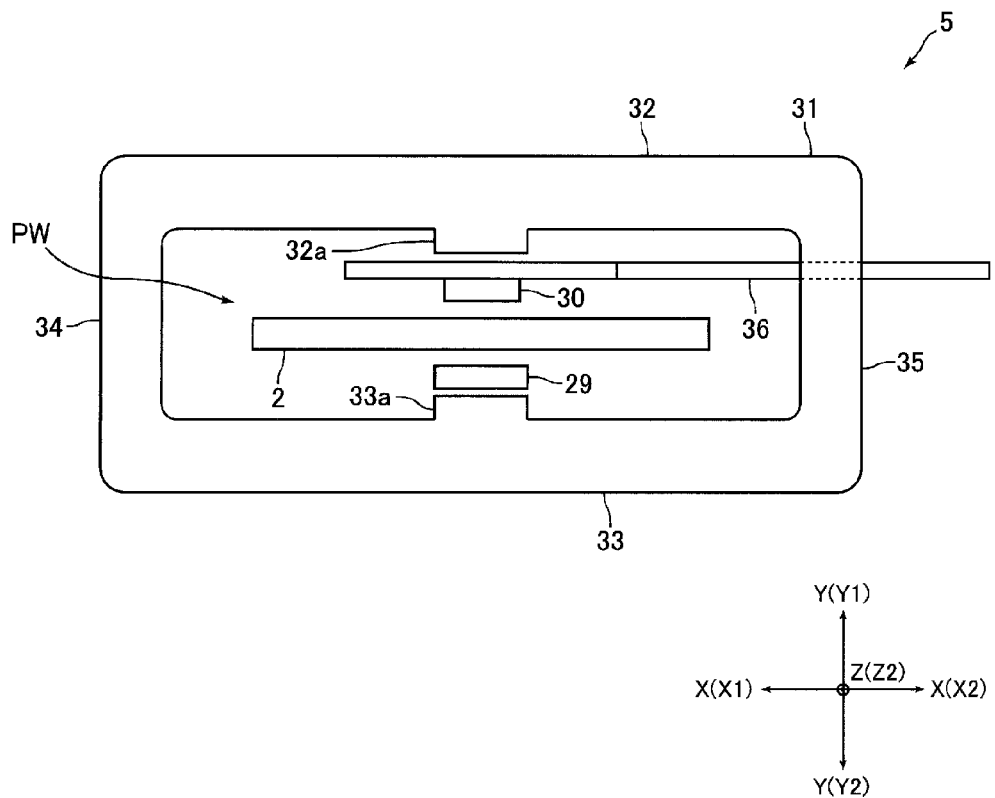
FIG. 7 is a plan view showing a second detection mechanism in FIG. 2.
Figure 8:
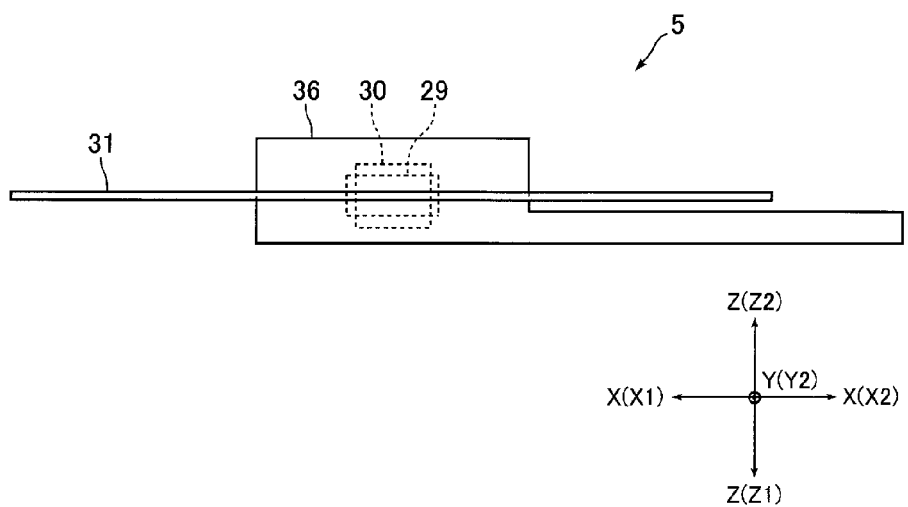
FIG. 8 is a side view showing the second detection mechanism in FIG. 2.

FIG. 4 is a perspective view showing a state that an excitation coil 8, a detection coil 9 and bobbins 20 and 21 are detached from a state shown in FIG. 3. FIG. 5 is a perspective view showing a ring-shaped core 11 in FIG. 3. FIG. 6 is a bottom view showing the ring-shaped core 11 in FIG. 3. FIG. 7 is a plan view showing the second detection mechanism 5 in FIG. 2. FIG. 8 is a side view showing the second detection mechanism 5 in FIG. 2.

The first detection mechanism 4 includes, as shown in FIGS. 3 and 4, an excitation coil 8, detection coils 9 and 10, and a ring-shaped core 11 around which the excitation coil 8 and the detection coils 9 and 10 are wound. The ring-shaped core 11 is formed of soft magnetic material. For example, the ring-shaped core 11 is formed of iron-based soft magnetic material such as ferrite, amorphous, Permalloy. Further, the ring-shaped core 11 is formed in a thin flat plate shape. For example, thickness of the ring-shaped core 11 is about 0.5 mm.

In this embodiment, the token discriminating device 1 is disposed so that a thickness direction of the ring-shaped core 11 and the upper and lower direction are coincided with each other and a token 2 is, as described above, passed through the passage PW from an upper side to a lower side. In other words, in this embodiment, a thickness direction of the ring-shaped core 11 and a passing direction of a token 2 are coincided with each other. Further, the front and rear direction is a thickness direction of a token 2 passing through the passage PW. The right and left direction in this embodiment is an orthogonal direction which is perpendicular to a passing direction of a token 2 and to a thickness direction of the token 2.

The ring-shaped core 11 is formed in a ring shape. Specifically, the ring-shaped core 11 is formed in a substantially rectangular ring shape which is long and thin in the right and left direction. The ring-shaped core 11 is structured of a substantially straight-shaped core 12 which structures a front side portion of the ring-shaped core 11 and is disposed in parallel to the right and left direction, a substantially straight-shaped core 13 which structures a rear side portion of the ring-shaped core 11 and is disposed in parallel to the core 12, a straight-shaped connecting core 14 which connects a right end of the core 12 with a right end of the core 13 and is disposed in parallel to the front and rear direction, and a straight-shaped connecting core 15 which connects a left end of the core 12 with a left end of the core 13 and is disposed in parallel to the connecting core 14. The ring-shaped core 11 in this embodiment is formed by press punching and the cores 12 and 13 and the connecting cores 14 and 15 are integrally formed with each other. In this embodiment, the core 12 is a fourth core and the core 13 is a third core.

The core 12 and the core 13 are formed in the same shape as each other and the connecting core 14 and the connecting core 15 are formed in the same shape as each other. Further, the ring-shaped core 11 is, as shown in FIG. 6, formed in a shape line-symmetrical with respect to the center line "CL1", which passes the center position of the ring-shaped core 11 in the front and rear direction and is parallel to the right and left direction, and is formed in a shape line-symmetrical with respect to the center line "CL2" which passes the center position of the ring-shaped core 11 in the right and left direction and is parallel to the front and rear direction.

The core 12 is formed with protruded parts 12a, 12b and 12c which are protruded toward the core 13 (in other words, toward a rear side). Front ends of the protruded parts 12a through 12c (in other words, base ends of the protruded parts 12a through 12c) are connected with a base part 12d of the core 12. The protruded parts 12a through 12c are formed in a rectangular shape. Rear end faces (in other words, tip end faces) of the protruded parts 12a through 12c are parallel to the right and left direction, and the right and left end faces of the protruded parts 12a through 12c are parallel to the front and rear direction. The rear end faces of the protruded parts 12a through 12c are disposed at the same positions as each other in the front and rear direction.

The protruded part 12a is disposed on a right end side, the protruded part 12b is disposed on a left end side, and the protruded part 12c is disposed between the protruded part 12a and the protruded part 12b. Specifically, the protruded part 12c is disposed so that the center of the protruded part 12c and the center of the core 12 are coincided with each other in the right and left direction, and the protruded part 12a and the protruded part 12b are disposed at positions line-symmetrical with the center line "CL2" as an axis of symmetry. The protruded part 12a and the protruded part 12b are formed in the same shape as each other and the core 12 is formed in a shape line-symmetrical with respect to the center line "CL2".

In the right and left direction, a gap space is formed between the protruded part 12a and the connecting core 14, and a gap space is formed between the protruded part 12b and the connecting core 15. Further, in the right and left direction, a gap space is formed between the protruded part 12a and the protruded part 12c, and a gap space is formed between the protruded part 12b and the protruded part 12c. Further, a rear end face 12e of the base part 12d between the protruded part 12a and the protruded part 12c and a rear end face 12f of the base part 12d between the protruded part 12b and the protruded part 12c are formed in a flat face shape which is perpendicular to the front and rear direction and are disposed at the same position in the front and rear direction. A rear end face 12g of the base part 12d between the protruded part 12a and the connecting core 14 and a rear end face 12h of the base part 12d between the protruded part 12b and the connecting core 15 are formed in a flat face shape which is perpendicular to the front and rear direction and are disposed at the same position in the front and rear direction. The rear end faces 12e and 12f are disposed on a front side relative to the rear end faces 12g and 12h.

As described above, the core 13 is formed in the same shape as the core 12 and is disposed at a position line-symmetrical with the center axis "CL1" as an axis of symmetry. The core 13 is formed with protruded parts 13a, 13b and 13c which are protruded toward the core 12 (in other words, toward a front side). Rear ends of the protruded parts 13a through 13c (in other words, base ends of the protruded parts 13a through 13c) are connected with a base part 13d of the core 13. The protruded parts 13a through 13c are formed in the same shape as the protruded parts 12a through 12c and front faces (in other words, tip end faces) of the protruded parts 13a through 13c are disposed at the same position in the front and rear direction.

In the right and left direction, the protruded part 13a is disposed at the same position as the protruded part 12a, the protruded part 13b is disposed at the same position as the protruded part 12b, and the protruded part 13c is disposed at the same position as the protruded part 12c. In other words, the protruded part 13a is protruded toward the protruded part 12a, the protruded part 13b is protruded toward the protruded part 12b, and the protruded part 13c is protruded toward the protruded part 12c. Similarly to the core 12, the core 13 is formed in a shape line-symmetrical with respect to the center line "CL2".

In the right and left direction, a gap space is formed between the protruded part 13a and the connecting core 14, and a gap space is formed between the protruded part 13b and the connecting core 15. Further, in the right and left direction, a gap space is formed between the protruded part 13a and the protruded part 13c, and a gap space is formed between the protruded part 13b and the protruded part 13c. Further, the front end face 13e of the base part 13d between the protruded part 13a and the protruded part 13c and the front end face 13f of the base part 13d between the protruded part 13b and the protruded part 13c are formed in a flat face shape which is perpendicular to the front and rear direction and are disposed at the same position in the front and rear direction. The front end face 13g of the base part 13d between the protruded part 13a and the connecting core 14 and the front end face 13h of the base part 13d between the protruded part 13b and the connecting core 15 are formed in a flat face shape which is perpendicular to the front and rear direction and are disposed at the same position in the front and rear direction. Further, the front end faces 13e and 13f are disposed on a rear side relative to the front end faces 13g and 13h.

A space between the protruded parts 12a through 12c and the protruded parts 13a through 13c in the front and rear direction is formed to be a part of the passage PW. The passage PW is formed in a rectangular shape which is long and thin in the right and left direction. As described above, the case body 3 is fixed with a guide member for guiding a token 2 to the passage opening 17a. The guide member guides a token 2 to the passage opening 17a so that the token 2 is passed between the right end faces of the protruded parts 12a and 13a and the left end faces of the protruded parts 12b and 13b. In other words, a distance "L1" in the right and left direction (see FIG. 6) between the right end faces of the protruded parts 12a and 13a and the left end faces of the protruded parts 12b and 13b is set to be equal to a width in the right and left direction of the passage PW. Further, the width in the right and left direction of the passage PW is set to be larger than an outer diameter of a token 2. In other words, the distance "L1" is larger than an outer diameter of a token 2. Specifically, the width in the right and left direction of the passage PW is set to be larger than an outer diameter of a token 2 having the largest outer diameter which is assumed to be inserted into a token inlet port of a slot machine. The distance "L1" is larger than an outer diameter of a token 2 having the largest outer diameter.

The protruded parts 12c and 13c are formed and disposed so that, when viewed in the front and rear direction, the entire protruded parts 12c and 13c are overlapped with a token 2 even in a case that the token 2 is passed at any position of the passage PW in the right and left direction. In other words, even when a token 2 is passed through the passage PW so that the right end faces of the protruded parts 12a and 13a or the left end faces of the protruded parts 12b and 13b are coincided with an outer peripheral end of the token 2, the protruded parts 12c and 13c are formed and disposed so that the entire protruded parts 12c and 13c are overlapped with the token 2 when viewed in the front and rear direction.

A distance "L2" between the protruded parts 12a through 12c and the protruded parts 13a through 13c in the front and rear direction (more specifically, distance "L2" between the rear end faces of the protruded parts 12a through 12c and the front end faces of the protruded parts 13a through 13c in the front and rear direction, see FIG. 6) is set to be shorter than a distance "L3" (see FIG. 6) between the right end faces of the protruded parts 12a and 13a and the left end face of the connecting core 14 in the right and left direction and shorter than a distance "L4" (see FIG. 6) between the left end faces of the protruded parts 12b and 13b and the right end face of the connecting core 15 in the right and left direction. Further, the distance "L2" between the protruded part 12c and the protruded part 13c in the front and rear direction is set to be shorter than the shortest distance between the protruded part 12c and the protruded part 13a (in other words, the shortest distance between the rear end of the right end face of the protruded part 12c and the front end of the left end face of the protruded part 13a) and shorter than the shortest distance between the protruded part 12c and the protruded part 13b (in other words, the shortest distance between the rear end of the left end face of the protruded part 12c and the front end of the right end face of the protruded part 13b).

A distance "L5" between the right end faces of the protruded parts 12a and 13a and the right end faces of the protruded parts 12b and 13b in the right and left direction is set to be smaller than an outer diameter of a token 2, and a distance "L6" between the left end faces of the protruded parts 12a and 13a and the left end faces of the protruded parts 12b and 13b in the right and left direction is set to be smaller than the outer diameter of the token 2. Specifically, the distances "L5" and "L6" are set to be smaller than an outer diameter of a token 2 having the smallest outer diameter which is assumed to be inserted into a token inlet port of a slot machine.

An excitation coil 8 is wound over the protruded parts 12a through 12c. Specifically, as shown in FIG. 3, the excitation coil 8 is wound over the protruded parts 12a through 12c through a bobbin 20 in a substantially rectangular tube shape which covers both upper and lower faces of the protruded parts 12a through 12c, the right end face of the protruded part 12a and the left end face of the protruded part 12b. In other words, the excitation coil 8 is wound over the protruded parts 12a through 12c through the bobbin 20 so that the protruded parts 12a through 12c are disposed on its inner peripheral side. A front end face of the bobbin 20 is abutted with the rear end faces 12g and 12h of the core 12. Further, terminal pins 23 are fixed to the bobbin 20. The excitation coil 8 is electrically connected with the terminal pins 23. The terminal pins 23 are protruded to a lower side and lower end sides of the terminal pins 23 are electrically connected and fixed to the circuit board 6.

A detection coil 9 is wound over the protruded parts 13a through 13c. Specifically, as shown in FIG. 3, the detection coil 9 is wound over the protruded parts 13a through 13c through a bobbin 21 in a substantially rectangular tube shape which covers both upper and lower faces of the protruded parts 13a through 13c, the right end face of the protruded part 13a and the left end face of the protruded part 13b. In other words, the detection coil 9 is wound over the protruded parts 13a through 13c through the bobbin 21 so that the protruded parts 13a through 13c are disposed on its inner peripheral side. A rear end face of the bobbin 21 is abutted with the front end faces 13g and 13h of the core 13. Further, terminal pins 24 are fixed to the bobbin 21. The detection coil 9 is electrically connected with the terminal pins 24. The terminal pins 24 are protruded to a lower side and lower end sides of the terminal pins 24 are electrically connected and fixed to the circuit board 6.

A detection coil 10 is wound around the protruded part 13c. Specifically, as shown in FIG. 4, the detection coil 10 is wound around the protruded part 13c through a bobbin 22 in a substantially rectangular tube shape which covers both upper and lower faces and both right and left end faces of the protruded part 13c. In other words, the detection coil 10 is wound around the protruded part 13c through the bobbin 22 so that the protruded part 13c is disposed on its inner peripheral side. A rear end face of the bobbin 22 is abutted with the front end faces 13e and 13f of the core 13. Further, terminal pins 25 are fixed to the bobbin 22. The detection coil 10 is electrically connected with the terminal pins 25. The terminal pins 25 are protruded to a lower side and lower end sides of the terminal pins 25 are electrically connected and fixed to the circuit board 6.

A second detection mechanism 5 includes a permanent magnet 29, a magnetic sensor 30 and a ring-shaped core 31 as a core body. The ring-shaped core 31 is, similarly to the ring-shaped core 11, formed of soft magnetic material. For example, the ring-shaped core 31 is formed of iron-based soft magnetic material such as ferrite, amorphous or Permalloy. The ring-shaped core 31 is formed in a flat thin plate shape and its thickness is about 0.5 mm. The ring-shaped core 31 is disposed so that its thickness direction and the upper and lower direction are coincided with each other and the thickness direction of the ring-shaped core 31 and a passing direction of a token 2 are coincided with each other.

The ring-shaped core 31 is formed in a ring shape. Specifically, the ring-shaped core 31 is formed in a substantially rectangular ring shape which is long and thin in the right and left direction. The ring-shaped core 31 is structured of a substantially straight-shaped core 32 structuring a front side portion of the ring-shaped core 31 and disposed in parallel to the right and left direction, a substantially straight-shaped core 33 structuring a rear side portion of the ring-shaped core 31 and disposed in parallel to the core 32, a straight-shaped connecting core 34 connecting a right end of the core 32 with a right end of the core 33 and disposed in parallel to the front and rear direction, and a straight-shaped connecting core 35 connecting a left end of the core 32 with a left end of the core 33 and disposed in parallel to the connecting core 34. The ring-shaped core 31 in this embodiment is formed by press punching and the cores 32 and 33 and the connecting cores 34 and 35 are integrally formed with each other. In this embodiment, the core 32 is a second core and the core 33 is a first core. Further, the connecting core 34 is a first connecting core and the connecting core 35 is a second connecting core.

The core 32 and the core 33 are formed in the same shape as each other and the connecting core 34 and the connecting core 35 are formed in the same shape as each other. When viewed in the upper and lower direction, the ring-shaped core 31 is disposed so that the center of the ring-shaped core 31 and the center of the ring-shaped core 11 are substantially coincided with each other. The ring-shaped core 31 is formed in a shape line-symmetrical with respect to the above-mentioned center line "CL1" and is formed in a shape line-symmetrical with respect to the above-mentioned center line "CL2".

The core 32 is formed with a protruded part 32a as a second protruded part which is protruded toward the core 33 (in other words, toward a rear side). The protruded part 32a is formed in a rectangular shape. A rear end face (in other words, a tip end face) of the protruded part 32a is parallel to the right and left direction, and right and left end faces of the protruded part 32a are parallel to the front and rear direction. Further, the protruded part 32a is disposed so that the center of the protruded part 32a in the right and left direction and the center of the core 32 are coincided with each other. The core 33 is formed with a protruded part 33a as a first protruded part which is protruded toward the core 32 (in other words, toward a front side). The protruded part 33a is formed in the same shape as the protruded part 32a. Further, the protruded part 33a is disposed at the same position as the protruded part 32a in the right and left direction. In other words, the protruded part 33a is protruded toward the protruded part 32a.

A permanent magnet 29 is formed in a substantially rectangular flat plate shape. The permanent magnet 29 is fixed to the case body 3 so that its thickness direction and the front and rear direction are coincided with each other. The permanent magnet 29 is magnetized so that a magnetic pole on its front face and a magnetic pole on its rear face are different from each other. The magnetic sensor 30 is one of a magnetoresistance effect element, a magnetic impedance element, a Hall element and a flux gate element. The magnetic sensor 30 is mounted on a circuit board 36. The circuit board 36 is fixed to the case body 3. The circuit board 36 is electrically connected with one end of a lead wire not shown. The other end of the lead wire is electrically connected with the circuit board 6.

The permanent magnet 29 and the magnetic sensor 30 are oppositely disposed to each other across the passage PW. In other words, a space between the permanent magnet 29 and the magnetic sensor 30 is a part of the passage PW. The permanent magnet 29 and the magnetic sensor 30 are disposed so that the center of the ring-shaped core 31 in the upper and lower direction and the centers of the permanent magnet 29 and the magnetic sensor 30 in the upper and lower direction are coincided with each other. Further, the permanent magnet 29 and magnetic sensor 30 are disposed so that the centers of the protruded parts 32a and 33a in the right and left direction and the centers of the permanent magnet 29 and the magnetic sensor 30 in the right and left direction are coincided with each other. Further, the permanent magnet 29 is disposed to a front side of the protruded part 33a and the magnetic sensor 30 is disposed to a rear side of the protruded part 32a through the circuit board 36. In other words, in the front and rear direction, the permanent magnet 29 is disposed between the passage PW and the protruded part 33a, and the magnetic sensor 30 is disposed between the passage PW and the protruded part 32a.

The first detection mechanism 4 is held by the case body 3 to a lower side of the upper face part 3a of the case body 3. As shown in FIG. 2, the case body 3 is formed with a bobbin abutting face 3d with which upper faces of the bobbins 20 and 21 are abutted and a core support face 3e which is capable of abutting with an outer peripheral side portion of the ring-shaped core 11 in flat face shapes perpendicular to the upper and lower direction. Further, relief parts 3g are formed on an inner side of the case body 3 for preventing the terminal pins 24 and 25 from interfering with the case body 3. The case body 3 is formed with a circuit board fixing face 3f to which the circuit board 6 is fixed in a flat face shape which is perpendicular to the upper and lower direction.

The second detection mechanism 5 is held by the case body 3 in an inside of a recessed part 3c of the upper face part 3a. In other words, the excitation coil 8, the detection coil 9 and the ring-shaped core 11 structuring the first detection mechanism 4 and the permanent magnet 29, the magnetic sensor 30 and the ring-shaped core 31 structuring the second detection mechanism 5 are held by the case body 3 at positions shifted from each other in the upper and lower direction. Further, the permanent magnet 29, the magnetic sensor 30 and the ring-shaped core 31 are disposed on an upstream side with respect to the excitation coil 8, the detection coil 9 and the ring-shaped core 11 in the passing direction of a token 2. A bottom face 3h of the recessed part 3c is formed in a flat face shape perpendicular to the upper and lower direction and an outer peripheral side portion of the ring-shaped core 31 is fixed to the bottom face 3h.

(Circuit Structure of Coin-Shaped Detection Object Discriminating Device)

Figure 9:
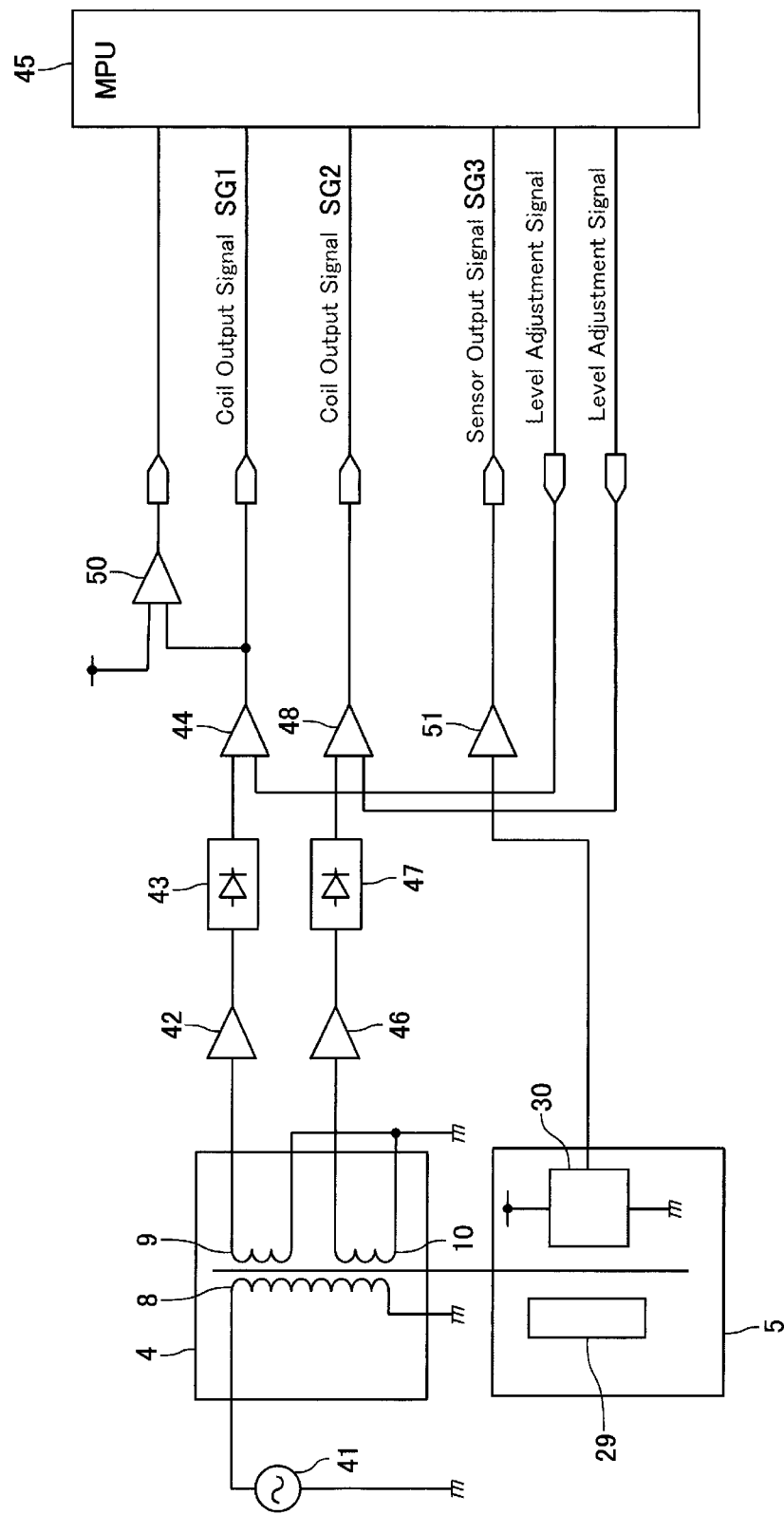
FIG. 9 is a block diagram showing a circuit diagram for the coin-shaped detection object discriminating device shown in FIG. 1.
Figure 10A:
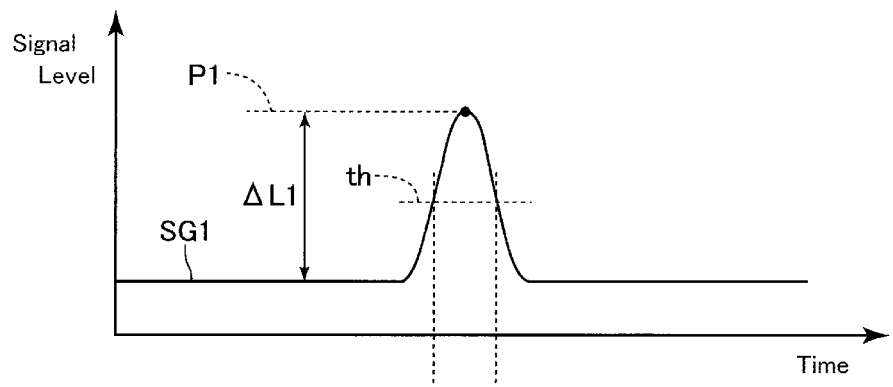
FIGS. 10(A), 10(B) and 10(C) are explanatory views showing coil output signals generated on the basis of outputs from detection coils and a sensor output signal generated on the basis of an output from a magnetic sensor shown in FIG. 9.
Figure 10B:
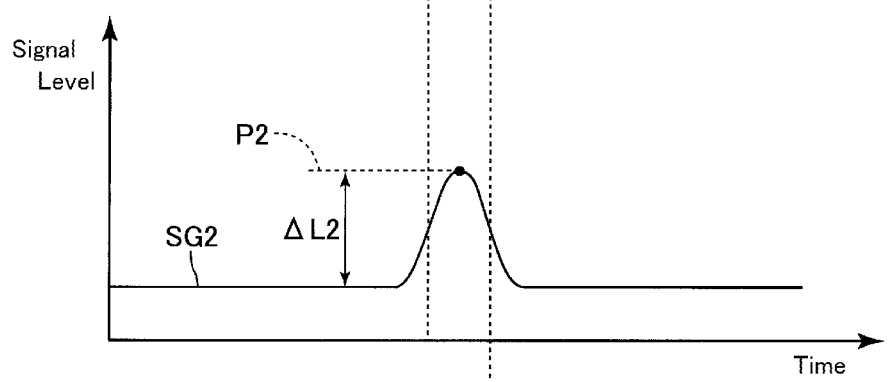
Figure 10C:
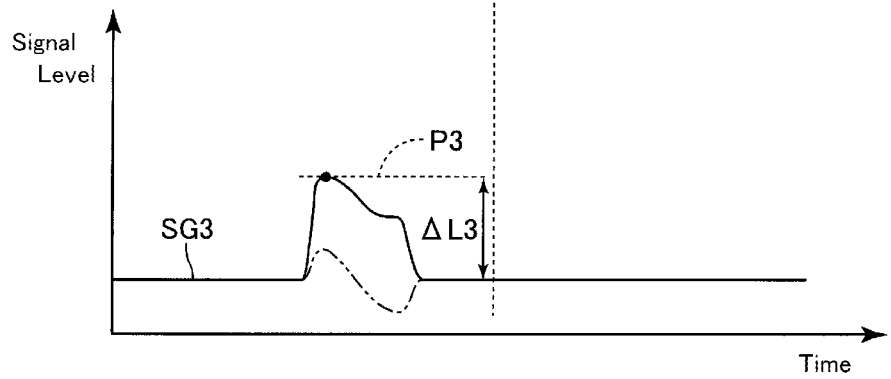
Figure 11A:
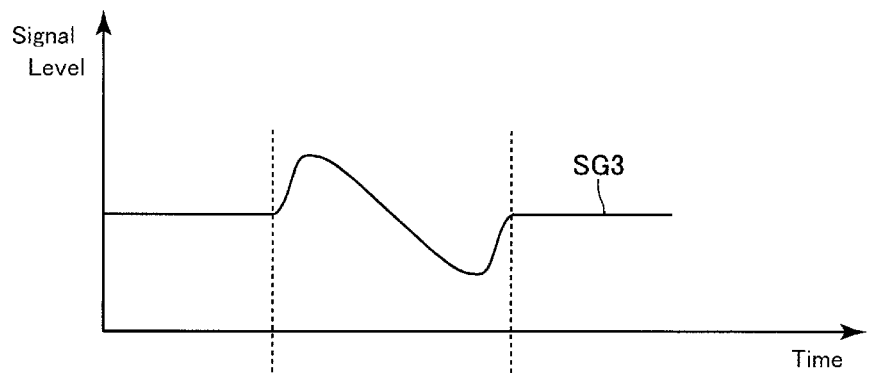
FIGS. 11(A), 11(B) and 11(C) are explanatory views showing sensor output signals generated on the basis of outputs from the magnetic sensor shown in FIG. 9.
Figure 11B:
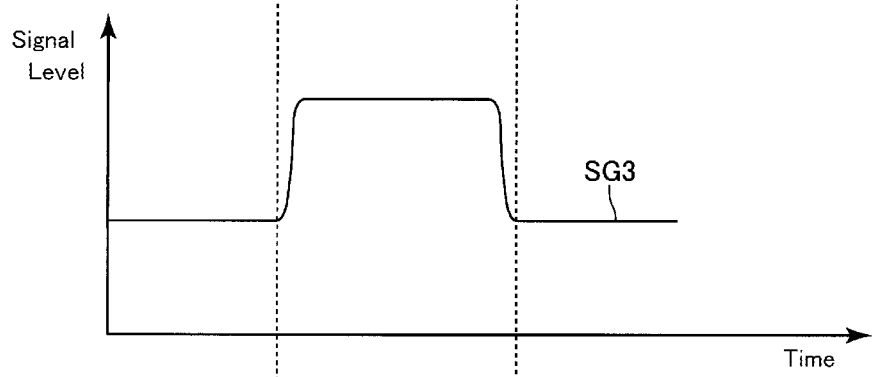
Figure 11C:
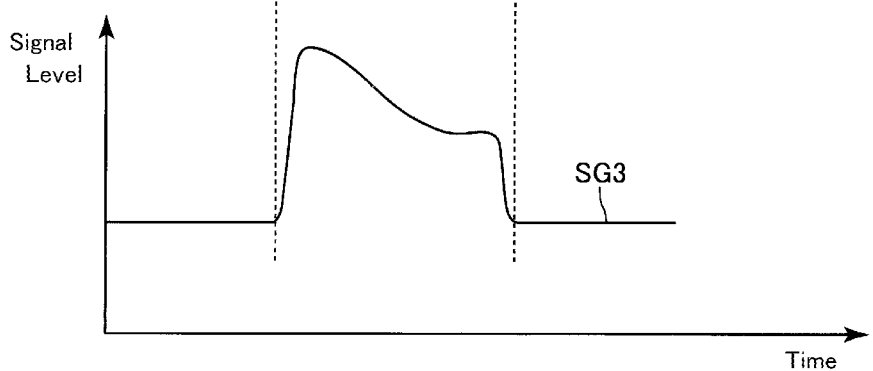

FIG. 9 is a block diagram showing a circuit diagram for the coin-shaped detection object discriminating device 1 shown in FIG. 1. FIGS. 10(A), 10(B) and 10(C) are explanatory views showing a coil output signal SG1 generated on the basis of an output from the detection coil 9, a coil output signal SG2 generated on the basis of an output from the detection coil 10, and a sensor output signal SG3 generated on the basis of an output from the magnetic sensor 30 shown in FIG. 9. FIGS. 11(A), 11(B) and 11(C) are explanatory views showing a sensor output signal SG3 generated on the basis of an output from the magnetic sensor 30 shown in FIG. 9.

As shown in FIG. 9, one end of a conducting wire structuring the excitation coil 8 is connected with an AC power source 41 and the other end of the conducting wire structuring the excitation coil 8 is grounded. One end of a conducting wire structuring the detection coil 9 is connected with an MPU (Micro Processing Unit) 45 as a control section through an amplifier circuit 42, a rectifier circuit 43 and a level adjustment circuit 44 and the other end of the conducting wire structuring the detection coil 9 is grounded. One end of a conducting wire structuring the detection coil 10 is connected with the MPU 45 through an amplifier circuit 46, a rectifier circuit 47 and a level adjustment circuit 48 and the other end of the conducting wire structuring the detection coil 10 is grounded. A comparator 50 is connected in parallel between the level adjustment circuit 44 and the MPU 45. Further, the magnetic sensor 30 is connected with the MPU 45 through an amplifier circuit 51. The amplifier circuits 42, 46 and 51, the rectifier circuits 43 and 47, the level adjustment circuits 44 and 48, the MPU 45 and the comparator 50 are mounted on the circuit board 6. In accordance with an embodiment of the present invention, the amplifier circuit 51 may be mounted on the circuit board 36.

In the first detection mechanism 4, when a token 2 is passed through the passage PW in a state that the excitation coil 8 generates an AC magnetic field to an inner peripheral side of the ring-shaped core 11 by electric power supplied from the AC power source 41, the AC magnetic field to the inner peripheral side of the ring-shaped core 11 is varied due to influence of an eddy current generated in the token 2 (in other words, by an eddy current loss). When the AC magnetic field to the inner peripheral side of the ring-shaped core 11 is varied, a level of an output from the detection coil 9 and a level of an output from the detection coil 10 are varied.

As described above, one end of the conducting wire structuring the detection coil 9 is connected with the MPU 45 through the amplifier circuit 42, the rectifier circuit 43 and the level adjustment circuit 44, and an analog-shaped coil output signal SG1 generated on the basis of the output from the detection coil 9 is inputted from the level adjustment circuit 44 into the MPU 45. Similarly, one end of the conducting wire structuring the detection coil 10 is connected with the MPU 45 through the amplifier circuit 46, the rectifier circuit 47 and the level adjustment circuit 48, and an analog-shaped coil output signal SG2 generated on the basis of the output from the detection coil 10 is inputted from the level adjustment circuit 48 into the MPU 45.

In this embodiment, the circuit of the token discriminating device 1 is structured so that, when a token 2 is passed through the passage PW in a state that the excitation coil 8 generates an AC magnetic field, the signal levels of the coil output signals SG1 and SG2 become larger. For example, when one token 2 is passed through the first detection mechanism 4, the coil output signals SG1 and SG2 whose signal levels are varied as shown in FIGS. 10(A) and 10(B) are inputted into the MPU 45.

As described above, the distance "L1" in the right and left direction between the right end faces of the protruded parts 12a and 13a and the left end faces of the protruded parts 12b and 13b are set to be equal to the width in the right and left direction of the passage PW and the detection coil 9 is wound over the protruded parts 13a through 13c through the bobbin 21 so as to cover both upper and lower faces of the protruded parts 13a through 13c, the right end face of the protruded part 13a and the left end face of the protruded part 13b. Therefore, a signal level of the coil output signal SG1 based on the output from the detection coil 9 is varied due to influence of material, thickness and an outer diameter of a token 2 which is passed through the first detection mechanism 4.

On the other hand, the protruded parts 12c and 13c are disposed between the protruded parts 12a and 13a and the protruded parts 12b and 13b and are formed and disposed so that, even when a token 2 is passed through at any position of the passage PW in the right and left direction, the entire protruded parts 12c and 13c are overlapped with the token 2 when viewed in the front and rear direction, and the detection coil 10 is wound around the protruded part 13c. Therefore, a signal level of the coil output signal SG2 based on an output from the detection coil 10 is mainly varied due to influence of material and thickness of the token 2 which is passed through the first detection mechanism 4.

Signal levels of the coil output signals SG1 and SG2 may be varied due to influence of variation of an ambient temperature around the token discriminating device 1. In this embodiment, in order to prevent signal levels of the coil output signals SG1 and SG2 from being deviated from a measurable range in the MPU 45 even when variation of an ambient temperature around the token discriminating device 1 or the like is occurred, the signal levels of the coil output signals SG1 and SG2 are adjusted regularly. Specifically, the level adjustment circuit 44 regularly adjusts a signal level of the coil output signal SG1 based on a level adjustment signal which is outputted from the MPU 45 based on the signal level of the coil output signal SG1 and is inputted into the level adjustment circuit 44. Further, the level adjustment circuit 48 regularly adjusts a signal level of the coil output signal SG2 based on a level adjustment signal which is outputted from the MPU 45 based on the signal level of the coil output signal SG2 and is inputted into the level adjustment circuit 48.

In this embodiment, the MPU 45 acquires signal values of the coil output signals SG1 and SG2 when a signal level of the coil output signal SG1 becomes a predetermined threshold value "th" or more. Specifically, first, a comparator 50 compares a signal level of the coil output signal SG1 inputted from the level adjustment circuit 44 with the threshold value "th" and the compared result is outputted to the MPU 45. Further, the MPU 45 acquires signal values of the coil output signals SG1 and SG2 when the signal level of the coil output signal SG1 is the threshold value "th" or more.

Material, thickness or a diameter is changed depending on a kind of token 2. Therefore, the peak value P1 of a signal level of the coil output signal SG1 and the peak value P2 of a signal level of the coil output signal SG2 may be varied depending on a kind of token 2 which is passed through the first detection mechanism 4. Therefore, the MPU 45 discriminates based on the peak value P1 and the peak value P2 whether or not material, thickness and a diameter of a token 2 which is passed through the first detection mechanism 4 are conformed with material, thickness and a diameter of a token 2 to be used in the slot machine on which the token discriminating device 1 is mounted.

Specifically, the MPU 45 judges that material, thickness and a diameter of a token 2 which is passed through the first detection mechanism 4 are conformed with material, thickness and a diameter of a token 2 to be used in the slot machine on which the token discriminating device 1 is mounted in a case that a difference "ΔL1" between a reference value which is a signal level of the coil output signal SG1 before a token 2 is passed through the first detection mechanism 4 and the peak value P1 is within a predetermined range and, in addition, that a difference "ΔL2" between a reference value which is a signal level of the coil output signal SG2 before the token 2 is passed through the ring-shaped core 11 and the peak value P2 is within a predetermined range. On the other hand, in a case that the "ΔL1" is out of the predetermined range or the "ΔL2" is out of the predetermined range, the MPU 45 judges that material, thickness and a diameter of a token 2 which is passed through the first detection mechanism 4 are not conformed with material, thickness and a diameter of a token 2 to be used in the slot machine on which the token discriminating device 1 is mounted.

As described above, the magnetic sensor 30 is connected with the MPU 45 through an amplifier circuit 51, and an analog-shaped sensor output signal SG3 generated on the basis of an output from the magnetic sensor 30 is inputted from the amplifier circuit 51 to the MPU 45. When a token 2 is passed through between the permanent magnet 29 and the magnetic sensor 30, an eddy current is generated in a metal token 2 due to influence of a DC magnetic field generated by the permanent magnet 29. In this case, a direction of an eddy current generated in a portion of a token 2 on an upper side relative to the permanent magnet 29 and a direction of an eddy current generated in a portion of the token 2 on a lower side relative to the permanent magnet 29 are opposite to each other. Therefore, when only influence of the eddy current is considered, in a case that one token 2 is passed through the second detection mechanism 5, a signal level of the sensor output signal SG3 is, for example, varied as shown in FIG. 11(A). In a case that only influence of an eddy current is considered, the peak value and the bottom value of a signal level of the sensor output signal SG3 are varied depending on a speed of a token 2 passing through the second detection mechanism 5.

When a token 2 having magnetism is passed through between the permanent magnet 29 and magnetic sensor 30, a DC magnetic field between the permanent magnet 29 and the magnetic sensor 30 is shielded and thus the DC magnetic field passing the magnetic sensor 30 is varied. In this embodiment, a circuit of the token discriminating device 1 is structured so that, when a token 2 having magnetism is passed through the DC magnetic field generated by the permanent magnet 29, a signal level of the sensor output signal SG3 becomes larger. Therefore, when only variation of the DC magnetic field is considered, in a case that one token 2 is passed through the second detection mechanism 5, a signal level of the sensor output signal SG3 is, for example, varied as shown in FIG. 11(B). Accordingly, when influence of an eddy current generated in the token 2 and variation of the DC magnetic field passing through the magnetic sensor 30 are considered, a signal level of the sensor output signal SG3 is, for example, varied as shown in FIG. 11(C).

As a result, when a nonmagnetic token 2 is passed through the second detection mechanism 5, for example, a sensor output signal SG3 whose signal level is varied as shown in FIG. 11(A) is inputted into the MPU 45. Further, when a token 2 having magnetism is passed through the second detection mechanism 5, for example, a sensor output signal SG3 whose signal level is varied as shown in FIG. 11(C) is inputted into the MPU 45. Therefore, the MPU 45 discriminates whether a token 2 passing through the second detection mechanism 5 is provided with magnetism or not based on the peak value P3 of a signal level of the sensor output signal SG3 (see FIG. 10(C)).

Specifically, the MPU 45 judges that a token 2 passing through the second detection mechanism 5 is a token 2 having magnetism in a case that the difference "ΔL3" between the reference value which is a signal level of the sensor output signal SG3 in a state that no token 2 is existed between the permanent magnet 29 and the magnetic sensor 30 and the peak value P3 is within the predetermined range. On the other hand, in a case that the "ΔL3" is out of the predetermined range, the MPU 45 judges that a token 2 passing through the second detection mechanism 5 is a nonmagnetic token 2. In a case that a nonmagnetic token 2 is passed through the second detection mechanism 5, if an external factor such as an ambient temperature around the token discriminating device 1 does not vary, a signal level of the sensor output signal SG3 when the centers of the permanent magnet 29 and the magnetic sensor 30 and the center of a token 2 are coincided with each other in the upper and lower direction becomes equal to a signal level of the sensor output signal SG3 when there is no token 2 between the permanent magnet 29 and the magnetic sensor 30.

As described above, the magnetic sensor 30 is disposed on an upper side relative to the detection coils 9 and 10. Therefore, when a token 2 is passed through the passage PW, as shown in FIGS. 10(A), 10(B) and 10(C), a signal level of the sensor output signal SG3 is varied ahead of signal levels of the coil output signals SG1 and SG2. In this embodiment, the first detection mechanism 4 and the second detection mechanism 5 are disposed so that a signal level of the coil output signal SG1 becomes not more than the threshold value "th" when a token 2 has completely passed through between the permanent magnet 29 and the magnetic sensor 30. Further, in this embodiment, a signal level of the sensor output signal SG3 when a signal level of the coil output signal SG1 becomes not more than the threshold value "th" is set to be a reference value. Based on a difference "ΔL3" between the reference value and the peak value P3, it is discriminated whether a token 2 passing through the second detection mechanism 5 is provided with magnetism or not.

As described above, the MPU 45 discriminates based on the "ΔL1" and the "ΔL2" whether material, thickness and a diameter of a token 2 which is passed through the first detection mechanism 4 are conformed with material, thickness and a diameter of a token 2 to be used in the slot machine on which the token discriminating device 1 is mounted or not. In addition, based on the "ΔL3", the MPU 45 discriminates whether the token 2 passing through the second detection mechanism 5 is provided with magnetism or not and thereby authenticity and a defective of the token 2 passing through the passage PW are discriminated.

In accordance with an embodiment of the present invention, the circuit of the token discriminating device 1 may be structured so that signal levels of the coil output signals SG1 and SG2 become smaller when a token 2 is passed through the first detection mechanism 4 in a state that the excitation coil 8 generates an AC magnetic field. In this case, for example, based on differences between the bottom values of signal levels of the coil output signals SG1 and SG2 and reference values, the MPU 45 discriminates whether or not material, thickness and a diameter of a token 2 which is passed through the first detection mechanism 4 are conformed with material, thickness and a diameter of a token 2 to be used in the slot machine on which the token discriminating device 1 is mounted. Further, in this case, for example, a signal level of the sensor output signal SG3 when a signal level of the coil output signal SG1 becomes not less than a predetermined threshold value is set to be a reference value. Based on a difference "ΔL3" between the reference value and the peak value P3, it is discriminated whether a token 2 passing through the second detection mechanism 5 is provided with magnetism or not.

The circuit of the token discriminating device 1 may be structured so that, when a token 2 having magnetism is passed through the DC magnetic field, a signal level of the sensor output signal SG3 (in other words, a signal level shown in FIG. 11(B)) in a case that only variation of the DC magnetic field is considered becomes smaller. In this case and, in a case that the circuit of the token discriminating device 1 is structured so that signal levels of the coil output signals SG1 and SG2 become larger when a token 2 is passed through the first detection mechanism 4 in a state that the excitation coil 8 generates an AC magnetic field, for example, a signal level of the sensor output signal SG3 when a signal level of the coil output signal SG1 becomes not more than the threshold value "th" is set to be a reference value and, based on a difference between the reference value and the bottom value of the sensor output signal SG3, it is discriminated whether the token 2 passing through the second detection mechanism 5 is provided with magnetism or not.

Further, in a case that the circuit of the token discriminating device 1 is structured so that, when a token 2 having magnetism is passed through the DC magnetic field, a signal level of the sensor output signal SG3 becomes smaller in a case that only variation of the DC magnetic field is considered and, in addition, in a case that the circuit of the token discriminating device 1 is structured so that signal levels of the coil output signals SG1 and SG2 become smaller when a token 2 is passed through the first detection mechanism 4 in a state that the excitation coil 8 generates an AC magnetic field, for example, a signal level of the sensor output signal SG3 when a signal level of the coil output signal SG1 becomes not less than a predetermined threshold value is set to be a reference value and, based on a difference between the reference value and the bottom value of the sensor output signal SG3, it is discriminated whether the token 2 passing through the second detection mechanism 5 is provided with magnetism or not.

(Principal Effects in this Embodiment)

As described above, in this embodiment, the permanent magnet 29 and the magnetic sensor 30 are oppositely disposed to each other across the passage PW. Therefore, according to this embodiment, a plurality of kinds of tokens whose outer diameters and thicknesses are the same but whose magnetic permeabilities are different from each other can be discriminated. For example, it is difficult to discriminate two kinds of tokens whose material, outer diameter and thickness are the same but one of which is provided with nickel plating on its surface and the other is provided with no nickel plating by using the first detection mechanism 4. However, according to this embodiment, the two kinds of tokens 2 can be discriminated by using the second detection mechanism 5.

In this embodiment, the ring-shaped core 31 is formed in a substantially rectangular ring shape. Further, in this embodiment, in the front and rear direction, the permanent magnet 29 is disposed between the passage PW and the protruded part 33a and the magnetic sensor 30 is disposed between the passage PW and the protruded part 32a. Therefore, according to this embodiment, leakage of magnetic flux generated from the permanent magnet 29 from the ring-shaped core 31 can be reduced and density of the magnetic flux generated from the permanent magnet 29 and passing through the magnetic sensor 30 can be increased through the protruded parts 32a and 33a. Accordingly, in this embodiment, a high degree of discrimination accuracy for a token 2 can be attained effectively.

In this embodiment, a signal level of the coil output signal SG1 based on an output from the detection coil 9 is varied due to influence of material, thickness and an outer diameter of a token 2 which is passed through the first detection mechanism 4. Further, a signal level of the coil output signal SG2 based on an output from the detection coil 10 is mainly varied due to influence of material and thickness of the token 2 passing through the first detection mechanism 4. Therefore, according to this embodiment, it is possible that an outer diameter of a token 2 is mainly discriminated by using the detection coil 9 and material and thickness of the token 2 are mainly discriminated by using the detection coil 10. Accordingly, in this embodiment, a high degree of discrimination accuracy for a token 2 can be attained.

Figure 12:
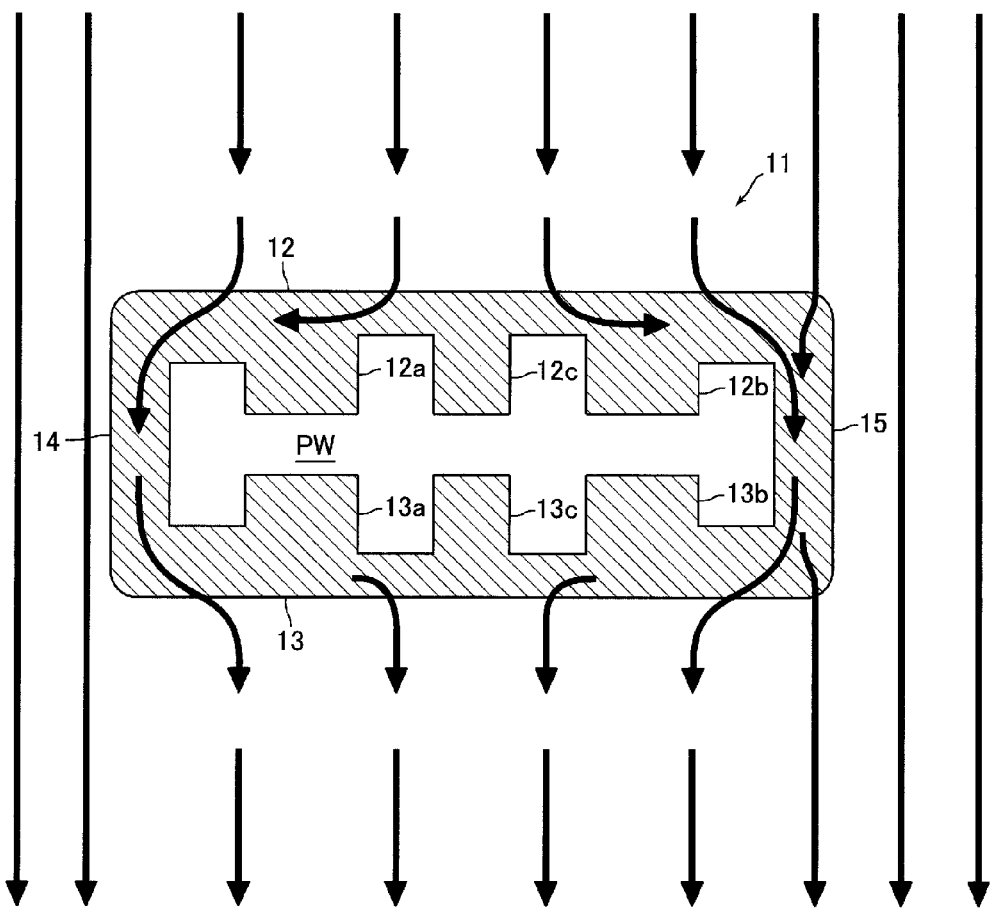
FIG. 12 is an explanatory view showing an effect of the coin-shaped detection object discriminating device shown in FIG. 1.
Figure 12:
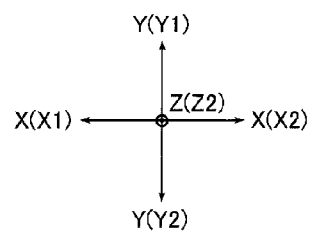

In this embodiment, the ring-shaped core 11 is formed in a substantially rectangular ring shape. Therefore, according to this embodiment, even when the token discriminating device 1 is disposed within an external magnetic field directing in an arbitrary direction in an "X-Y" plane structured of the "X" direction and the "Y" direction, the magnetic path caused by the external magnetic field is not formed in the passage PW between the protruded parts 12a through 12c and the protruded parts 13a through 13c. For example, even when the token discriminating device 1 is disposed within an external magnetic field in which magnetic lines of force are directed to the rear direction (arrows shown in FIG. 12), magnetic paths caused by the external magnetic field are not formed between the protruded parts 12a through 12c and the protruded parts 13a through 13c in the passage PW as shown in FIG. 12. Similarly, in this embodiment, the ring-shaped core 31 is formed in a substantially rectangular ring shape and thus, even when the token discriminating device 1 is disposed within an external magnetic field directing in an arbitrary direction in the "X-Y" plane, magnetic path caused by the external magnetic field is not formed between the permanent magnet 29 and the magnetic sensor 30 in the passage PW. In other words, according to this embodiment, the ring-shaped cores 11 and 31 can be functioned as a magnetic shield and, as a result, lowering of discrimination accuracy for a token 2 caused by an external magnetic field around the token discriminating device 1 can be suppressed. In this embodiment, even when the token discriminating device 1 is disposed within an external magnetic field directing in the upper and lower direction ("Z" direction), the upper and lower direction is perpendicular to sensing directions of the detection coils 9 and 10 and the magnetic sensor 30 and thus the token discriminating device 1 is hard to be affected by the external magnetic field.

In this embodiment, the first detection mechanism 4 and the second detection mechanism 5 are held by the common case body 3. Therefore, according to this embodiment, a structure of the token discriminating device 1 can be simplified.

In this embodiment, the first detection mechanism 4 and the second detection mechanism 5 are disposed so that, when a signal level of the coil output signal SG1 becomes not more than the threshold value "th", a token 2 has completely passed through between the permanent magnet 29 and the magnetic sensor 30. Further, in this embodiment, a signal level of the sensor output signal SG3 when a signal level of the coil output signal SG1 becomes not more than the threshold value "th" is set to be a reference value and, based on a difference "ΔL3" between the reference value and the peak value P3, it is discriminated whether the token 2 passing through the second detection mechanism 5 is provided with magnetism or not. In other words, in this embodiment, a token 2 is discriminated by using the magnetic sensor 30 based on a difference "ΔL3" between a value of the sensor output signal SG3 immediately after the token 2 has passed between the permanent magnet 29 and the magnetic sensor 30 and the peak value P3. Therefore, according to this embodiment, even when a signal level of the sensor output signal SG3 in a standby state that no token 2 is existed between the permanent magnet 29 and the magnetic sensor 30 is varied due to variation of ambient temperature around the token discriminating device 1, the variation can be canceled and, as a result, a token 2 can be discriminated with a high degree of accuracy.

(Modified Embodiment of Second Detection Mechanism)

Figure 13:
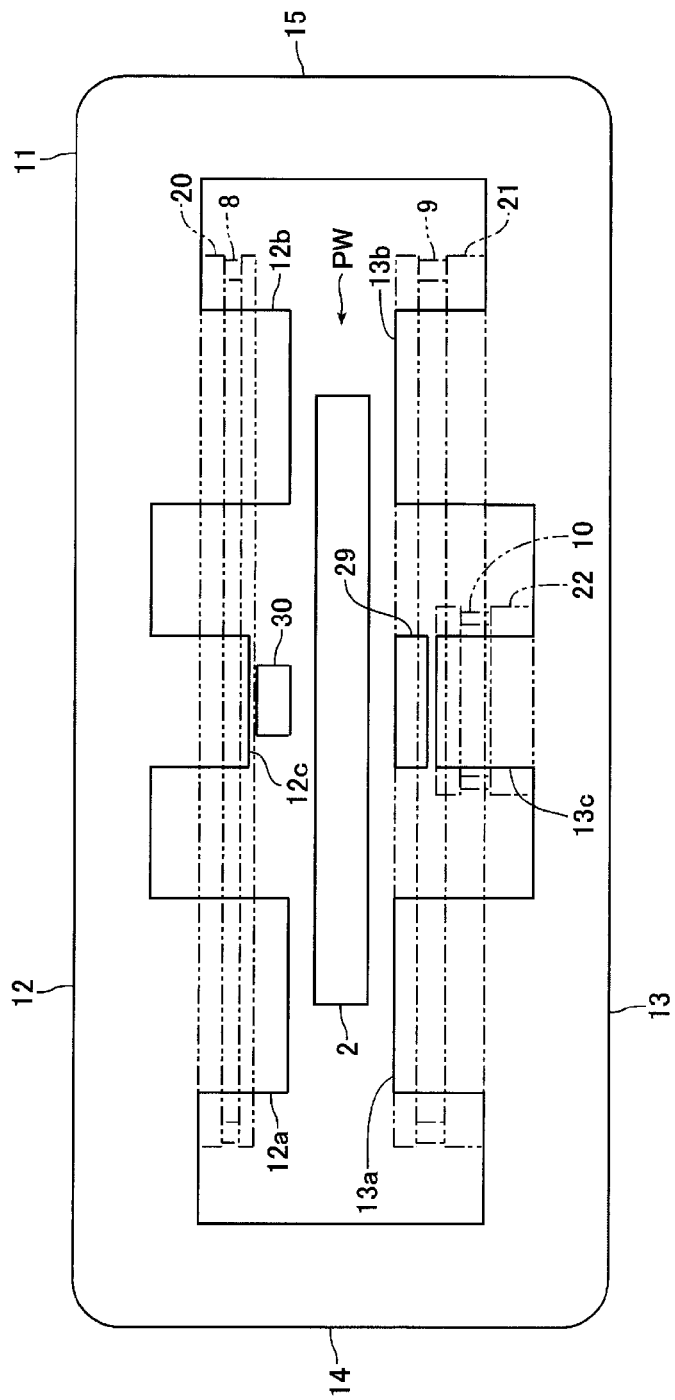
FIG. 13 is an explanatory bottom view showing a coin-shaped detection object discriminating device in accordance with another embodiment of the present invention.
Figure 13:
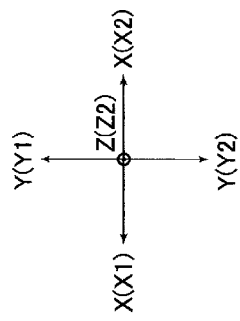
Figure 14A:
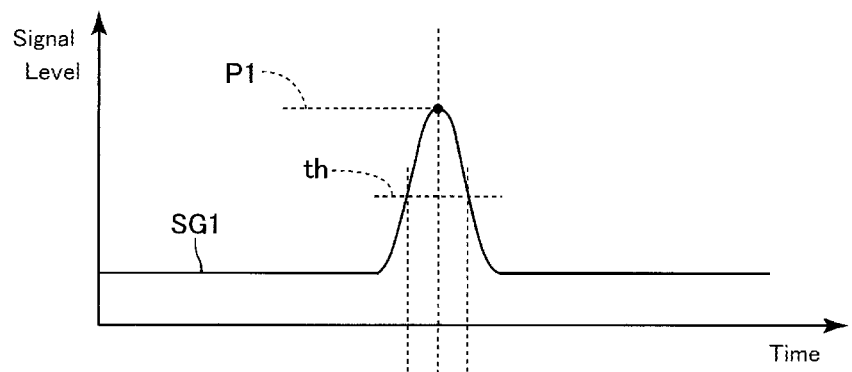
FIGS. 14(A), 14(B) and 14(C) are explanatory views showing coil output signals and a sensor output signal in the coin-shaped detection object discriminating device shown in FIG. 13.
Figure 14B:
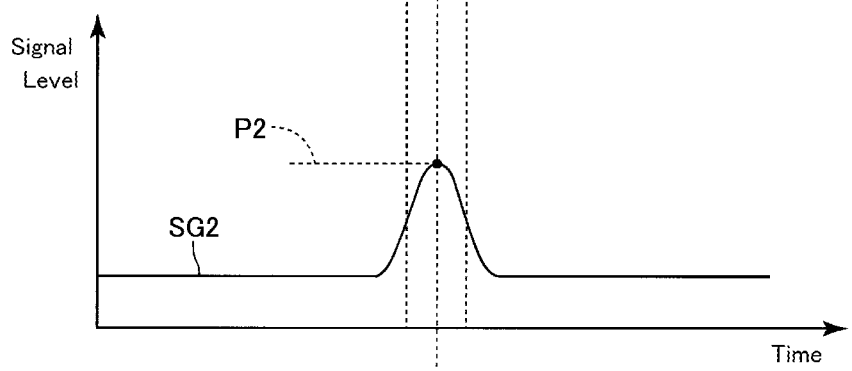
Figure 14C:
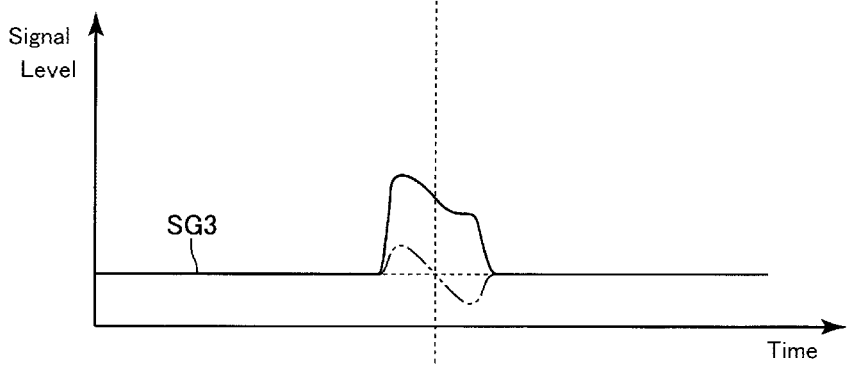

FIG. 13 is an explanatory bottom view showing a token discriminating device 1 in accordance with another embodiment of the present invention. FIGS. 14(A), 14(B) and 14(C) are explanatory views showing coil output signals SG1 and SG2 and a sensor output signal SG3 in the token discriminating device 1 shown in FIG. 13.

In the embodiment described above, the ring-shaped core 31 is separately provided from the ring-shaped core 11, and the permanent magnet 29 is disposed between the protruded part 33a formed in the ring-shaped core 31 and the passage PW and the magnetic sensor 30 is disposed between the protruded part 32a formed in the ring-shaped core 31 and the passage PW. However, the present invention is not limited to this embodiment. For example, as shown in FIG. 13, it may be structured that the permanent magnet 29 is disposed between the protruded part 13c formed in the ring-shaped core 11 and the passage PW and the magnetic sensor 30 is disposed between the protruded part 12c formed in the ring-shaped core 11 and the passage PW. In other words, it may be structured that the permanent magnet 29 and the magnetic sensor 30 are disposed so that a center in the upper and lower direction of the ring-shaped core 11 and the centers in the upper and lower direction of the permanent magnet 29 and the magnetic sensor 30 are coincided with each other, so that the centers in the right and left direction of the protruded parts 12c and 13c and the centers in the right and left direction of the permanent magnet 29 and the magnetic sensor 30 are coincided with each other, and so that the permanent magnet 29 is disposed to a front side of the protruded part 13c and the magnetic sensor 30 is disposed to a rear side of the protruded part 12c.

In this case, no ring-shaped core 31 is required to be provided separately from the ring-shaped core 11 and thus a structure of the token discriminating device 1 can be simplified. Further, in this case, the ring-shaped core 11 is a core body, the core 12 is the second core, the core 13 is the first core, the connecting core 14 is the first connecting core, and the connecting core 15 is the second connecting core. Further, the protruded part 12c is the second protruded part, the protruded part 13c is the first protruded part, the protruded parts 12a and 12b are the fourth protruded part, and the protruded parts 13a and 13b are the third protruded part.

In this case, it is preferable that the MPU 45 discriminates a token 2 by using the magnetic sensor 30 based on a value of the sensor output signal SG3 at the time of a peak of a signal level of the coil output signal SG1. In the modified embodiment shown in FIG. 13, when the centers of the permanent magnet 29 and the magnetic sensor 30 and the center of a token 2 is coincided with each other in the upper and lower direction, the center of the detection coil 9 and the center of the token 2 are coincided with each other in the upper and lower direction. Therefore, when the centers of the permanent magnet 29 and the magnetic sensor 30 and the center of a token 2 are coincided with each other in the upper and lower direction, a signal level of the coil output signal SG1 becomes a peak. Further, as described above, in a case that a nonmagnetic token 2 is passed between the permanent magnet 29 and the magnetic sensor 30, when there is no variation of an external factor such as ambient temperature around the token discriminating device 1, a value of the sensor output signal SG3 when the centers of the permanent magnet 29 and the magnetic sensor 30 and the center of the token 2 are coincided with each other in the upper and lower direction becomes equal to a value of the sensor output signal SG3 in a state that no token 2 is existed between the permanent magnet 29 and the magnetic sensor 30.

Therefore, when the MPU 45 acquires a value of the sensor output signal SG3 at a standby time immediately before or immediately after a token 2 has passed between the permanent magnet 29 and the magnetic sensor 30, even in a case that a peak value and a bottom value of a signal level of the sensor output signal SG3 when only influence of an eddy current is considered is varied depending on a speed of the token 2 passing through the second detection mechanism 5, the MPU 45 is capable of discriminating whether the token 2 is provided with magnetism or not on the basis of whether or not a signal level of the sensor output signal SG3 at the time of a peak of a signal level of the coil output signal SG1 is equal to a signal level of the sensor output signal SG3 at the standby time (see FIGS. 14(A), 14(B) and 14(C)). Accordingly, discrimination whether a token 2 is provided with magnetism or not can be performed further easily.

In the modified embodiment shown in FIG. 13 and FIGS. 14(A), 14(B) and 14(C), a low-pass filter is disposed between the amplifier circuit 51 and the MPU 45 and a sensor output signal SG3 after having passed through the low-pass filter is inputted into the MPU 45. Further, in a case that a circuit of the token discriminating device 1 is structured so that a signal level of the coil output signal SG1 becomes smaller when a token 2 is passed through the first detection mechanism 4 in a state that the excitation coil 8 generates an AC magnetic field, the token 2 is discriminated by using the magnetic sensor 30 based on a value of the sensor output signal SG3 at the time of a bottom value of a signal level of the coil output signal SG1.

In the modified embodiment shown in FIG. 13, the detection coil 10 may be omitted. In this case, a low-pass filter and a high-pass filter are disposed in parallel between the amplifier circuit 51 and the MPU 45 and, based on the sensor output signal after having passed through the high-pass filter and the coil output signal SG1, it may be discriminated whether or not material, thickness and a diameter of a token 2 passing through the passage PW are conformed with material, thickness and a diameter of a token 2 to be used in the slot machine on which the token discriminating device 1 is mounted.

(Other Embodiments)

Although the present invention has been shown and described with reference to a specific embodiment, various changes and modifications will be apparent to those skilled in the art from the teachings herein.

In the embodiment described above, the token discriminating device 1 includes the first detection mechanism 4 and the second detection mechanism 5. However, the present invention is not limited to this embodiment. For example, the token discriminating device 1 may include only the second detection mechanism 5. Further, in the embodiment described above, it is discriminated whether a token 2 is provided with magnetism or not by using the second detection mechanism 5. However, a difference of magnetic permeabilities of a plurality of kinds of tokens 2 having magnetism may be discriminated by using the second detection mechanism 5. Further, in the embodiment described above, the first detection mechanism 4 and the second detection mechanism 5 are held by a common case body 3. However, the first detection mechanism 4 and the second detection mechanism 5 may be held by case bodies separately formed from each other.

In the embodiment described above, the MPU 45 discriminates whether a token 2 passing through the second detection mechanism 5 is provided with magnetism or not based on a difference "ΔL3" between a reference value of the sensor output signal SG3 and the peak value P3. However, the present invention is not limited to this embodiment. For example, the MPU 45 may discriminates whether a token 2 passing through the second detection mechanism 5 is provided with magnetism or not based on an absolute value of the peak value P3.

In the embodiment described above, the cores 32 and 33 and the connecting cores 34 and 35 are integrally formed with each other. However, the present invention is not limited to this embodiment. For example, at least one of the cores 32 and 33 and the connecting cores 34 and 35 is separately formed and remaining cores 32 and 33 and the connecting cores 34 and 35 may be integrated with each other. Further, the ring-shaped core 31 may be, for example, structured of a metallic foil which is formed of magnetic material and a thin reinforcing plate made of resin on which the metallic foil is stuck. Similarly, at least one of the cores 12 and 13 and the connecting cores 14 and 15 is separately formed and remaining cores 12 and 13 and the connecting cores 14 and 15 may be integrated with each other. Further, the ring-shaped core 11 may be, for example, structured of a metallic foil which is formed of magnetic material and a thin reinforcing plate made of resin on which the metallic foil is stuck.

In the embodiment described above, the second detection mechanism 5 includes the ring-shaped core 31 formed in a ring shape but the second detection mechanism 5 may include no ring-shaped core 31. Further, the second detection mechanism 5 may include, instead of the ring-shaped core 31, a core body formed with a gap (separated portion) in at least one of the cores 32 and 33 and the connecting cores 34 and 35. In this case, the gap may be filled with nonmagnetic material. Similarly, the first detection mechanism 4 may include, instead of the ring-shaped core 11, a core body formed with a gap (separated portion) in at least one of the cores 12 and 13 and the connecting cores 14 and 15. Further, in the embodiment described above, the ring-shaped cores 11 and 31 are formed in a substantially rectangular ring shape. However, the ring-shaped cores 11 and 31 may be formed in a circular ring shape, an elliptical ring shape or a long elliptically annular ring shape or may be formed in a multi-angular ring aside other than a rectangular ring shape.

In the embodiment described above, the token discriminating device 1 is mounted and used in a slot machine. However, the present invention is not limited to this embodiment. For example, the token discriminating device 1 may be mounted and used in a token vending machine and a token counting machine. Further, in the embodiment described above, the token discriminating device 1 for discriminating a token 2 which is used in a slot machine is described as an example for a coin-shaped detection object discriminating device in accordance with an embodiment of the present invention. However, a coin-shaped detection object discriminating device to which at least an embodiment of the present invention is applied may be, for example, a device for discriminating other coin-shaped detection objects such as a token used in a game machine. Further, a coin-shaped detection object in at least an embodiment of the present invention is not limited to a token used in a slot machine or a game machine and it may be a coin. A token vending machine is a device into which cash is inserted to purchase tokens and it is installed between slot machines or in an entrance of a hall. A token counting machine is a device for counting the number of tokens collected from respective slot machines. One token counting machine is, for example, disposed for a predetermined number of slot machines (for example, installed in each island) and a token counting machine counts the number of tokens 2 collected from a plurality of slot machines structuring an island where the token counting machine is installed. Further, a token counting machine may be, for example, a totally centralized processing machine which further collects tokens 2 which are collected in respective islands to count the total number. Further, a token counting machine may be, for example, a device for counting the number of tokens 2 to exchange the tokens 2 with a gift.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

The invention claimed is:

1. A coin-shaped detection object discriminating device for use with a detection object in a coin shape, the coin-shaped detection object discriminating device comprising:
   a passage through which the detection object is passed;
   a permanent magnet;
   a magnetic sensor disposed opposite to the permanent magnet across the passage;
   an excitation coil;
   a detection coil;
   a third core formed of soft magnetic material which is disposed on one side in the thickness direction of the detection object and around which one of the excitation coil and the detection coil is wound; and
   a forth core formed of soft magnetic material which is disposed on the other side in the thickness direction of the detection object and around which the other of the excitation coil and the detection coil is wound.

2. The coin-shaped detection object discriminating device according to claim 1, further comprising a core body formed of soft magnetic material which is provided with a first core disposed on one side in a thickness direction of the detection object passing through the passage and a second core disposed on an other side in the thickness direction of the detection object,
   wherein the first core is formed with a first protruded part which is protruded toward the second core,
   wherein the second core is formed with a second protruded part which is protruded toward the first protruded part,
   wherein the permanent magnet is disposed between the passage and the first protruded part in the thickness direction of the detection object, and
   wherein the magnetic sensor is disposed between the passage and the second protruded part in the thickness direction of the detection object.

3. The coin-shaped detection object discriminating device according to claim 2, wherein
   when a direction perpendicular to a passing direction of the detection object and the thickness direction of the detection object is referred to as an orthogonal direction,
   the core body is formed in a ring shape which is provided with the first core, the second core, a first connecting core connecting one end of the first core with one end of the second core in the orthogonal direction, and a second connecting core connecting the other end of the first core with the other end of the second core in the orthogonal direction.

4. The coin-shaped detection object discriminating device according to claim 3, wherein the magnetic sensor is one of a magnetoresistance effect element, a magnetic impedance element, a Hall element and a flux gate element.

5. The coin-shaped detection object discriminating device according to claim 1, further comprising a case body in which the permanent magnet, the magnetic sensor, the excitation coil, the detection coil, the third core and the fourth core are accommodated,
   wherein the excitation coil, the detection coil, the third core and the fourth core are held by the case body at a shifted position from the permanent magnet and the magnetic sensor in a passing direction of the detection object.

6. The coin-shaped detection object discriminating device according to claim 5, further comprising a control section which is connected with the magnetic sensor and the detection coil,
   wherein the magnetic sensor is disposed on an upstream side relative to the detection coil in the passing direction of the detection object,
   wherein a sensor output signal in an analog shape generated on a basis of an output of the magnetic sensor and a coil output signal in an analog shape generated on a basis of an output of the detection coil are inputted into the control section, wherein in a case that a signal level of the coil output signal becomes larger when the detection object is passed through the passage, the control section discriminates the detection object by using the magnetic sensor based on a difference between one of a peak value and a bottom value of the sensor output signal and a value of the sensor output signal when a signal level of the coil output signal becomes not more than a predetermined threshold value, and wherein in a case that a signal level of the coil output signal becomes smaller when the detection object is passed through the passage, the control section discriminates the detection object by using the magnetic sensor based on a difference between one of a peak value and a bottom value of the sensor output signal and a value of the sensor output signal when a signal level of the coil output signal becomes not less than a predetermined threshold value.

7. The coin-shaped detection object discriminating device according to claim 2, further comprising:
an excitation coil which is wound around one of the first protruded part and the second protruded part, and
a detection coil which is wound around the other of the first protruded part and the second protruded part.

8. The coin-shaped detection object discriminating device according to claim 7, wherein
when a direction perpendicular to a passing direction of the detection object and the thickness direction of the detection object is referred to as an orthogonal direction,
a third protruded part which is protruded toward the second core is formed on both sides in the orthogonal direction of the first protruded part of the first core,
a fourth protruded part which is protruded toward the third protruded part is formed on both sides in the orthogonal direction of the second protruded part of the second core,
a first detection coil as the detection coil is wound over the first protruded part and the third protruded parts,
a second detection coil as the detection coil is wound around the first protruded part, and
the excitation coil is wound over the second protruded part and the fourth protruded parts.

9. The coin-shaped detection object discriminating device according to claim 7, further comprising a control section which is connected with the magnetic sensor and the detection coil,
wherein a sensor output signal in an analog shape generated on a basis of an output of the magnetic sensor and a coil output signal in an analog shape generated on a basis of an output of the detection coil are inputted into the control section, wherein in a case that a signal level of the coil output signal becomes larger when the detection object is passed through the passage, the control section discriminates the detection object by using the magnetic sensor based on a value of the sensor output signal at a time of a peak of the signal level of the coil output signal, and wherein in a case that a signal level of the coil output signal becomes smaller when the detection object is passed through the passage, the control section discriminates the detection object by using the magnetic sensor based on a value of the sensor output signal at a time of a bottom of the signal level of the coil output signal.

10. A coin-shaped detection object discriminating device for use with a detection object in a coin shape, the coin-shaped detection object discriminating device comprising:
a passage through which the detection object is passed;
a permanent magnet;
a magnetic sensor disposed opposite to the permanent magnet across the passage; and
a core body formed of soft magnetic material which is provided with a first core disposed on one side in a thickness direction of the detection object passing through the passage and a second core disposed on an other side in the thickness direction of the detection object,
wherein the first core is formed with a first protruded part which is protruded toward the second core,
wherein the second core is formed with a second protruded part which is protruded toward the first protruded part,
wherein the permanent magnet is disposed between the passage and the first protruded part in the thickness direction of the detection object, and
wherein the magnetic sensor is disposed between the passage and the second protruded part in the thickness direction of the detection object.

* * * * *